United States Patent [19]
Aharoni et al.

[11] Patent Number: 5,280,723
[45] Date of Patent: Jan. 25, 1994

[54] APPARATUS AND METHOD FOR DATA ACQUISITION AND PROCESSING

[75] Inventors: Abraham Aharoni, Rehovot; Tzach Livne, Ramat-Gan; Itzhack Segev, Holon, all of Israel

[73] Assignee: IRT Inspection Research & Technologies, Inc., Israel

[21] Appl. No.: 591,745

[22] Filed: Oct. 2, 1990

[30] Foreign Application Priority Data

Oct. 8, 1989 [IL] Israel .................................. 91929

[51] Int. Cl.$^5$ ............................................. G01N 29/10
[52] U.S. Cl. ..................................... 73/602; 364/507; 73/588
[58] Field of Search ................. 73/602, 588, 618, 620; 364/507

[56] References Cited

U.S. PATENT DOCUMENTS

| | | | |
|---|---|---|---|
| 4,412,248 | 10/1983 | Carmen | 73/602 |
| 4,655,228 | 4/1987 | Shimura et al. | 73/602 |
| 4,750,366 | 6/1988 | Nicolas | 73/602 |
| 4,799,387 | 1/1989 | Matsuo | 73/620 |

*Primary Examiner*—Hezron E. Williams
*Assistant Examiner*—Rose M. Finley
*Attorney, Agent, or Firm*—Anthony J. Casella; Gerald E. Hespos

[57] ABSTRACT

There is provided a programmable receiver for detecting signals reflected from, or transmitted through, a material for analyzing flaws in the material, having a circuit for dividing the signals into a multiplicity of separate, independent sections for selective evaluation of waveform portions as contained in each of the sections. A method for detecting and analyzing flaws in materials is also provided.

11 Claims, 26 Drawing Sheets

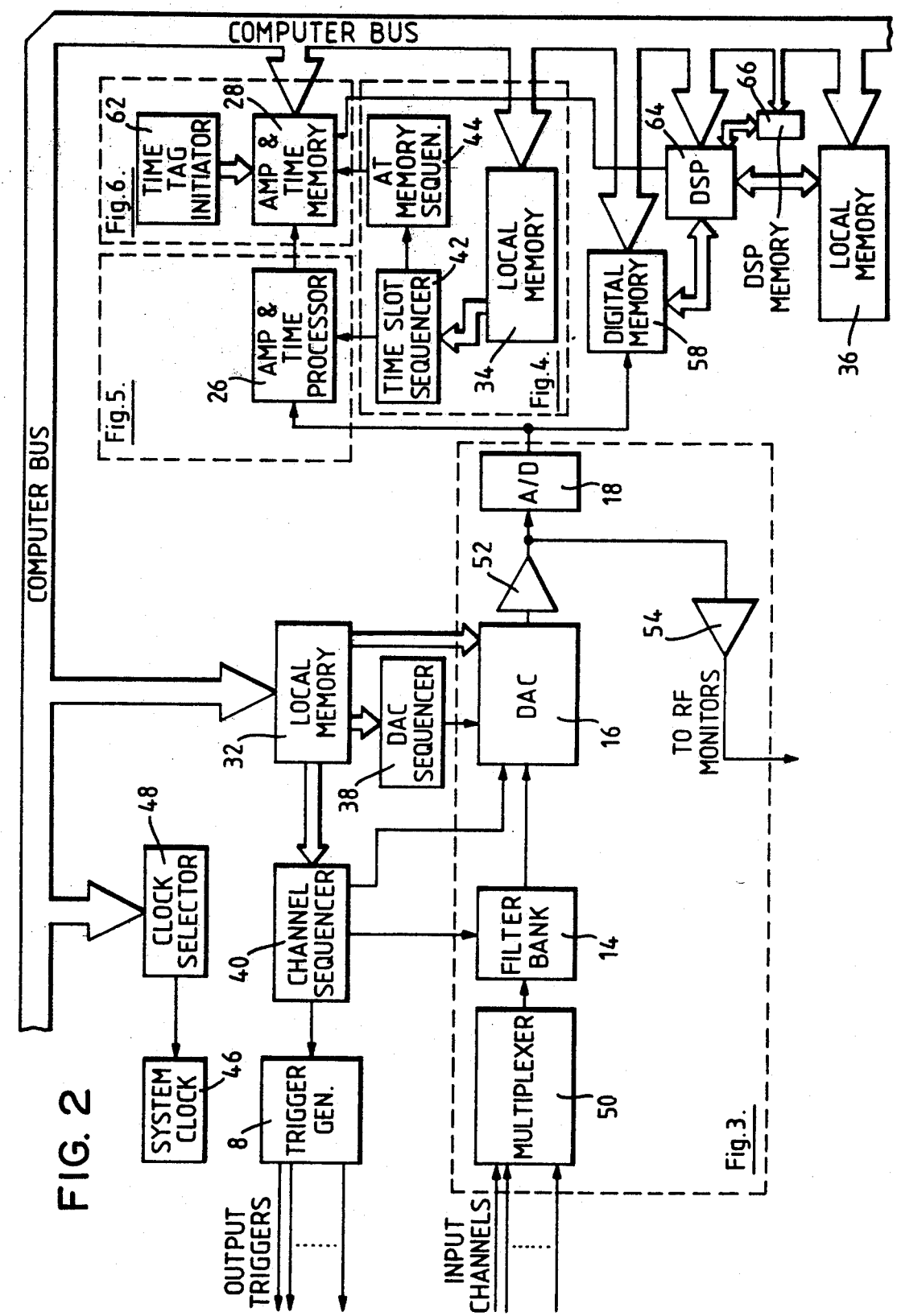

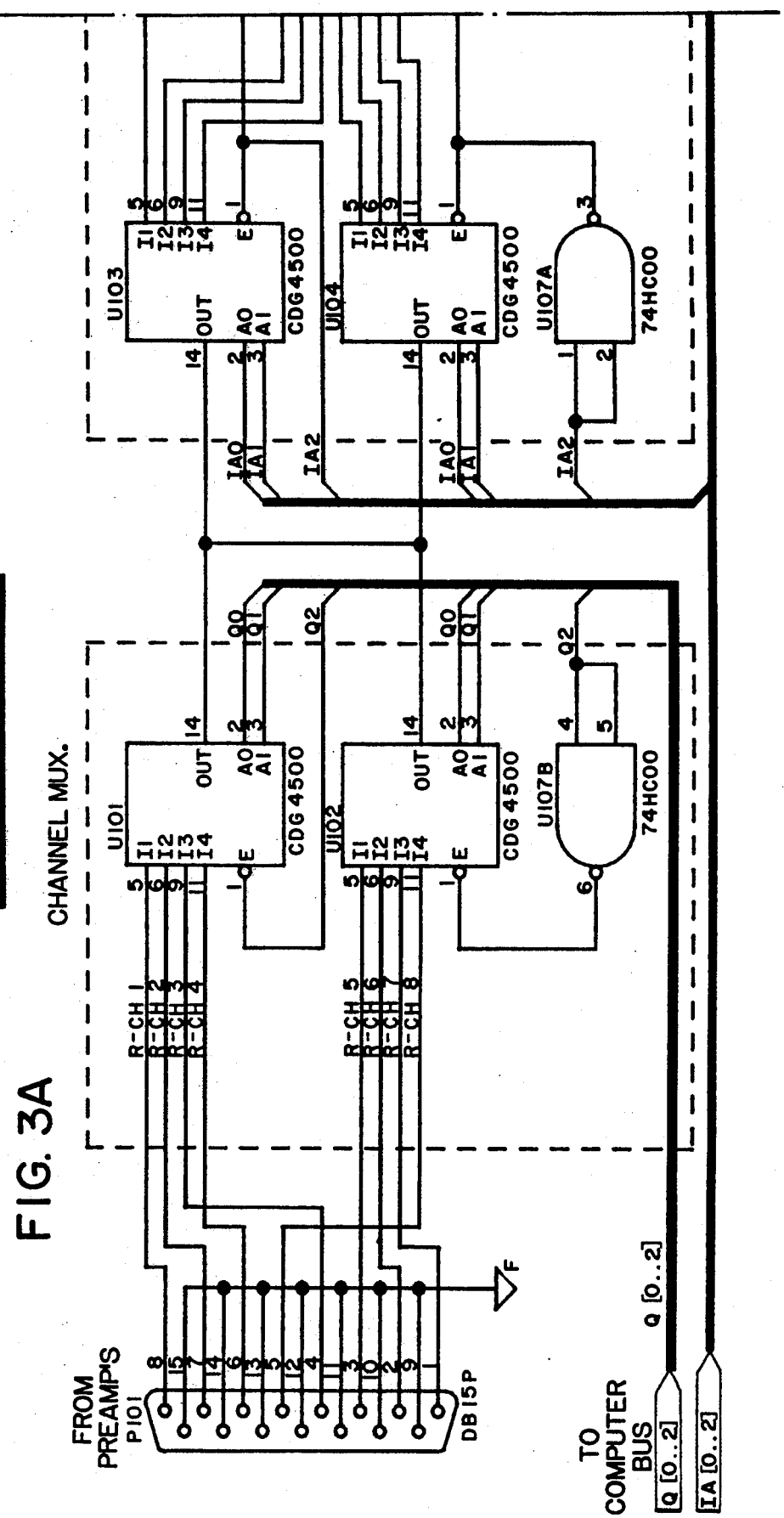

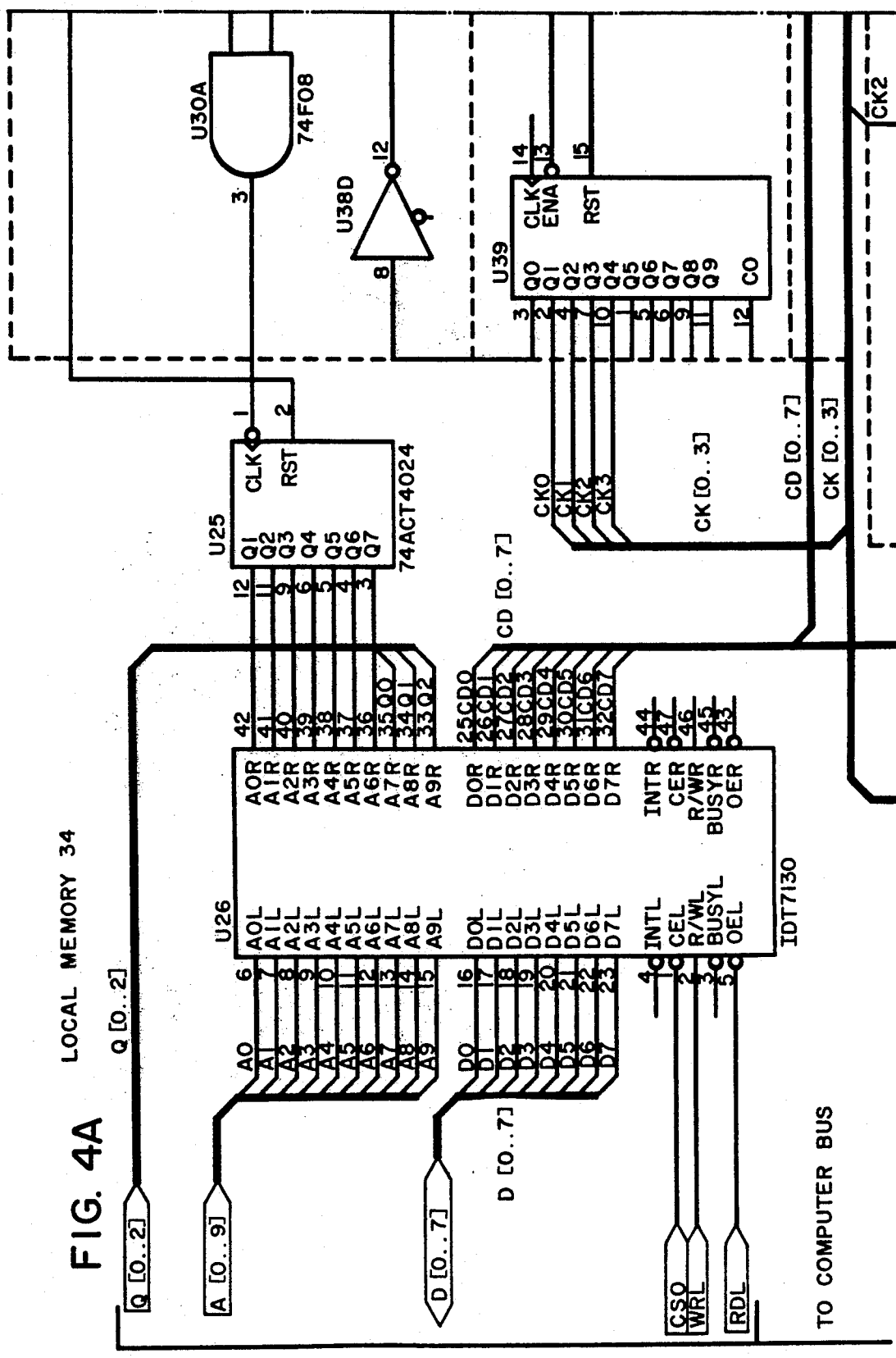

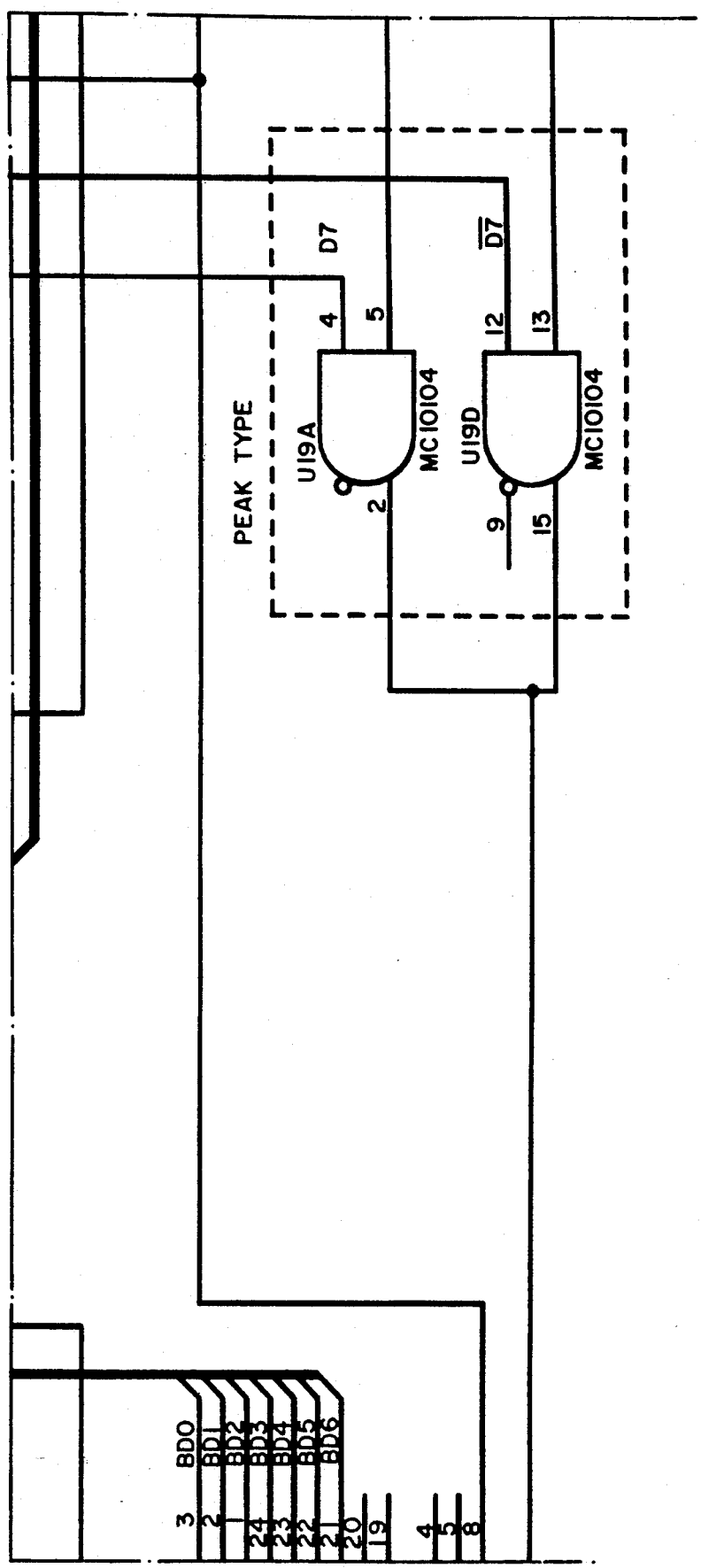

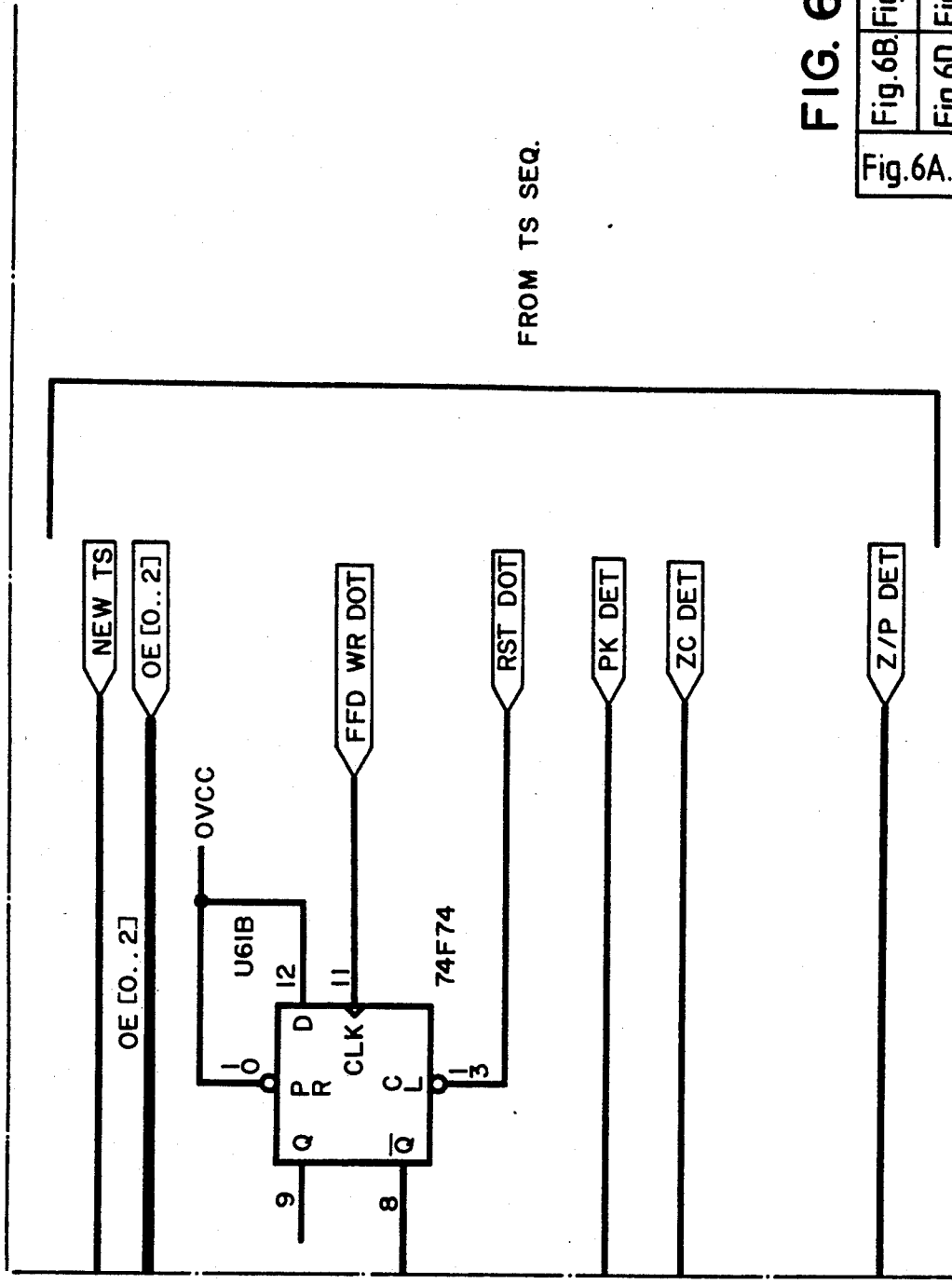

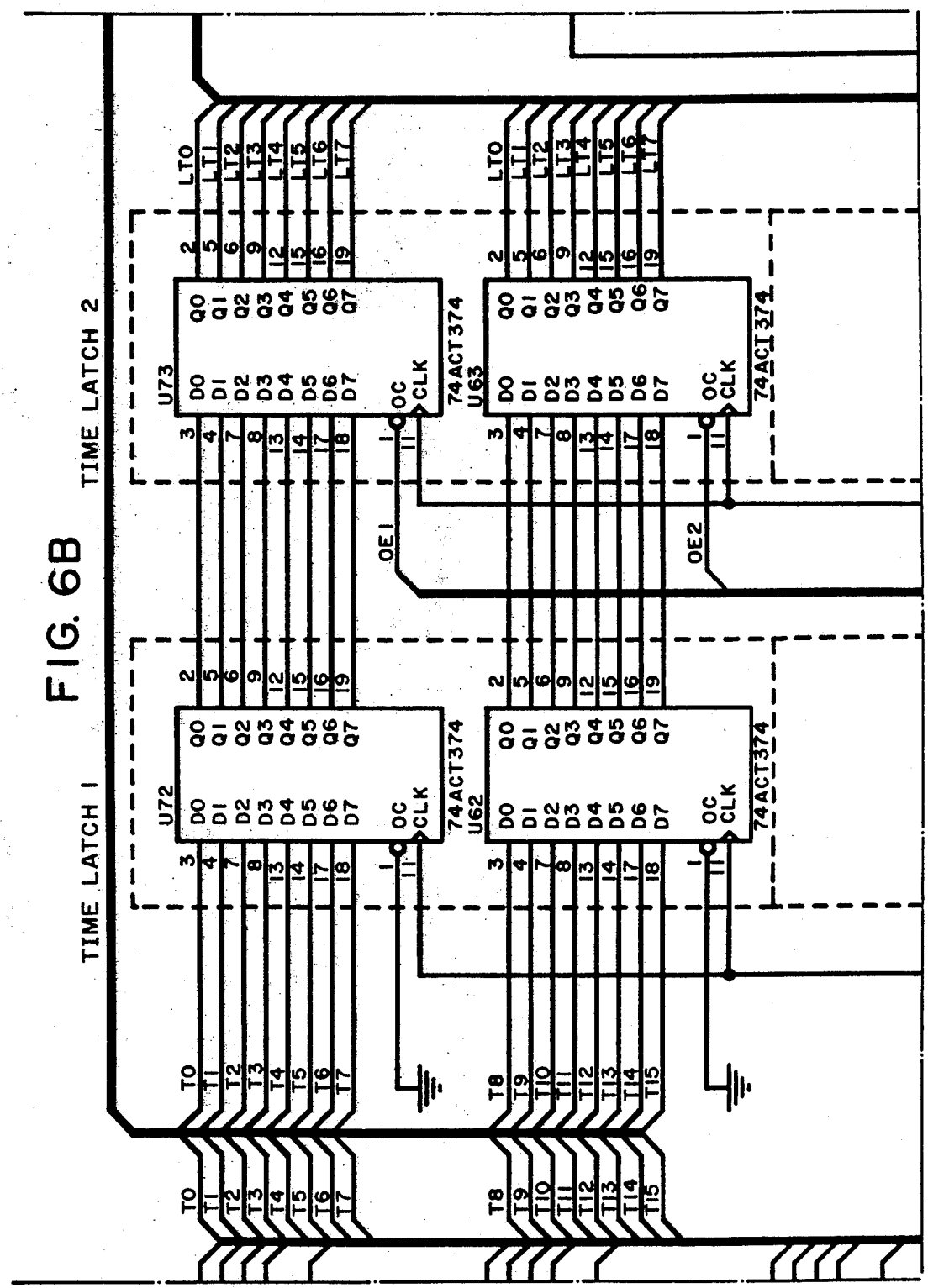

APPARATUS AND METHOD FOR DATA ACQUISITION AND PROCESSING

The present invention relates to an apparatus and method for data acquisition and processing and in particular to real time signal data acquisition and processing. The invention is utilisable in various fields including on-line process control and non-destructive testing and inspecting procedures.

In non-destructive, testing mapping reflected or transmitted amplitudes of a signal incident on a test piece, is frequently required. Classical application of the technique involves detection of the peak material echo in the pulse echo (PE) mode or identification of signal fading in through transmission (TT) mode. In a former method a time gate is defined to distinguish from reflections internal to the material, which result from flaws, and the front and back-wall reflections. A similar gate is used in the TT mode to eliminate the effect of spurious reflections. These basic techniques, along with many variants, have served to detect internal flaws in metals, plastics and composite materials and parts over the last years. Modern non-destructive testing requirements also include flaw characterization and classification for complete assessment of parts and material quality and for providing useful feedback to the design and production process.

Modern scanners store on hardware memory the signal amplitude collected at each measurement point (pixel) along the scan. The stored data can then be recalled for display and printout, as well as for further processing, whenever an improved indication of the flawed regions is required.

Although detected signals passing through the material in the PE or TT modes indicate the presence of flaws of practical interest, such signals may be ambiguous in the sense that different flaw types can generate identical signatures. Therefore, and in particular on expensive components, detected flaws must be verified, and evaluated in order to avoid erroneous rejection of the test piece. Traditionally this task was performed manually by an expert through examination of the signature of the flawed region. Ambiguities in interpretation lead sometimes to the need for repeating the scan with variation to the initial setup. Recent progress in electronic digitizing equipment permits recording of the entire signal waveform corresponding to a detection time gate at every pixel and storing of this information for display and processing. The very fine detail recorded with this method is typically sufficient to characterize flaws in post-scan processing, either by automatic algorithms or through manual analysis. This approach improves the confidence of identification while substantially simplifying the characterization procedure, as well as relaxing requirements on operator skills and training.

The massive data handled in recording the fully digitized signal as described above, is the main drawback of this method. For example, on a medium size airfoil section, 5 m long by 2 m wide, there would typically be some 2,500,000 pixels (resolution 2×2 mm). Assuming a material depth of 25 mm, digitized at 0.1 mm depth increments, this would amount to 625 Mega Bytes of data. Three practical limitations result as a consequence of this large data volume: in the acquisition process the data transfer rate normally limits the scanning speed, considerably increasing the overall scan time; storage, display and post-scan processing are slowed down, entailing prolonged flaw evaluation procedures; and super-large mass storage devices must be provided for both active memory and archival storage, which is used for future reference.

The Programmable Receiver (PR) of the present invention is based on the consideration of the raw data signal in sections, namely, the signal is divided into separate, independent sections, called Time Slots, which Time Slots enable an operator to utilize this device to meet almost any task in non-destructive testing. The operator can consider each section of the signal separately and award it a suitable treatment. For instance, where only the peak amplitude and its time occurrence are of interest, the system can calculate these values in real time without affecting the setup in any of the other Time Slots, and where more complex analysis is required, the full signal waveform is recorded throughout a Time Slot to capture all signal details for post-processing. There is no conceptual limit on the number of Time Slots in which a peak is sought. This is contrary to current practice in which separate hardware processing channels for each peak detection are required, or alternatively, in which postprocessing algorithms must be employed for identification of such signal features. This versatility of utilizing the Time Slots, permits the optimization of the most crucial test parameters, i.e., test speed and information content. Current inspection systems do not provide such capability, since they are normally limited to operation in either a two gate mode or a full digitization mode.

The use of a multitude of Time Slots permits piecewise definition of the information to be recorded along the depth of the material. For example, the first Time Slot can be assigned to record the amplitude of the echo from the wall of the material, the second to record the peak of any echo in the first layer of the material, the third to record the full wave reflection from the second layer (which may be problematic) and so on. The Time Slots are in principle unlimited in number and with their aid, highly intricate recording procedures can be devised. It is noted that more elaborate processing of the waveform section in each may be implemented by incorporating additional computation power on-board. Such processing can include Fourier analysis, Deconvolution and other signal reconstructive algorithms.

A further feature of the present invention provides the ability to perform multiple peak and Time Tagging (assignment of a time value to the peak) processes on a single data record. In many prior art instruments a Time Tag is recorded for each peak detected in a prespecified time-gate. This information is used to indicate the depth of the flaw associated with this peak. A similar Time Tag is provided in the present invention with an additional feature. The Time Tag can be programmed to indicate the time associated with the peak in a given Time Slot, or the time associated with the zero-crosing following the particular peak. The signal zero-crossing can be selected on positive or negative signal slopes. This feature offers improved material thickness measurement capabilities, which are best performed by such zero-crossing measurements. Furthermore, the ability to select the slope of the zero-crossing permits compensation for reflected signal polarity reversal. In this case, time intervals between a positive slope zero-crossing on the reference signal and the negative slope zero-crossing on the inverted signal can be used.

The method and device of the present invention is designed to combine in a single apparatus the speed and streamline storage requirements of standard flaw detection methods with the versatility and refinements of full wave recording. By incorporating additional on-board processing power, it is possible to perform many signal processing tasks for more difficult analysis applications. Alternatively, since it is found that under 4-5% of a scanned area is defective, it is possible to separate the flaw detection process from the flaw characterization process which can both be implemented with the same device. This separation can take effect by first scanning the material with a simple analysis to locate the flaws, then repeating the scan on the localized defective region while reprogramming the PR for full wave recording, which can then be analyzed off-line. The result is optimization of both scan time and data volume.

It is therefore a broad object of the present invention to provide a detector for multiple peak detection in a single signal channel.

It is a further object to provide a method and programmable receiver for detecting and analysing flaws in a material.

In accordance with the present invention, there is therefore provided a programmable receiver for detecting signals reflected from, or transmitted through, a material for analysing flaws in said material, comprising circuit means for dividing said signals into a multiplicity of separate, independent sections for selective evaluation of waveform portions as contained in each of said sections.

The invention further provides a method for detecting and analysing flaws in materials, comprising the steps of transmitting signals towards a material, receiving signals reflected from, or transmitted through, said material and dividing said received signals into a multiplicity of separate independent sections for selective evaluation of waveform portions as contained in each of said sections.

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 2 is a more detailed block diagram of the diagram of FIG. 1;

FIGS. 3 and 3A-3E are circuit diagrams of the preamplifiers, the input selector, the filter bank, DAC and A/D converter shown in FIGS. 1 and 2;

FIGS. 4 and 4A-4F are circuit diagrams of the Time Slot sequencer, time and amplitude sequencer, and of part of the local memory of FIGS. 1 and 2;

FIGS. 5 and 5A-5F are circuit diagrams of the time and amplitude processor;

FIGS. 6 and 6A-6E are circuit diagrams of the Time Tag and time and amplitude memory of FIG. 2;

Figure 1:
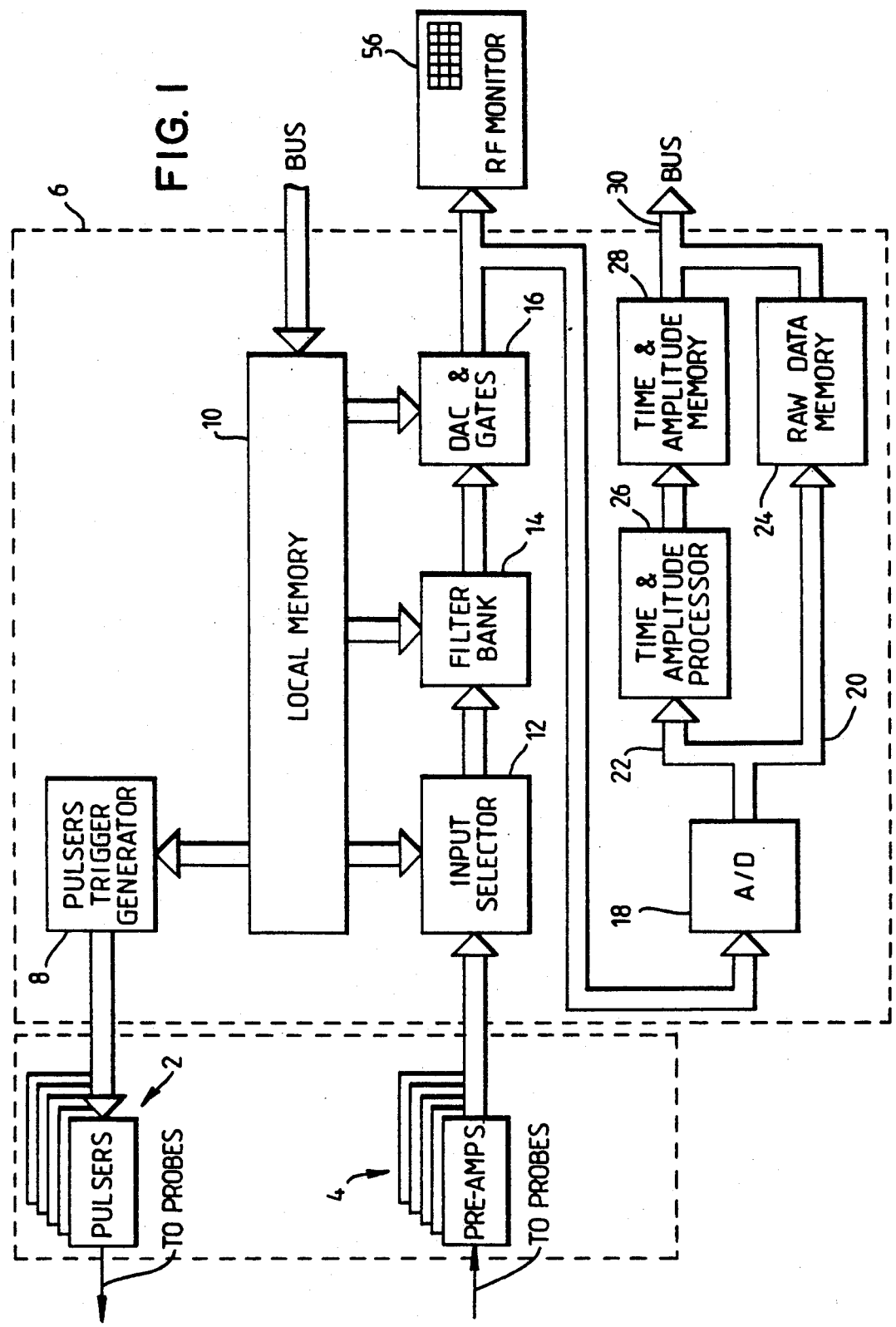
FIG. 1 is a block diagram of the data acquisition and processing device according to the invention.
Figure 3B:
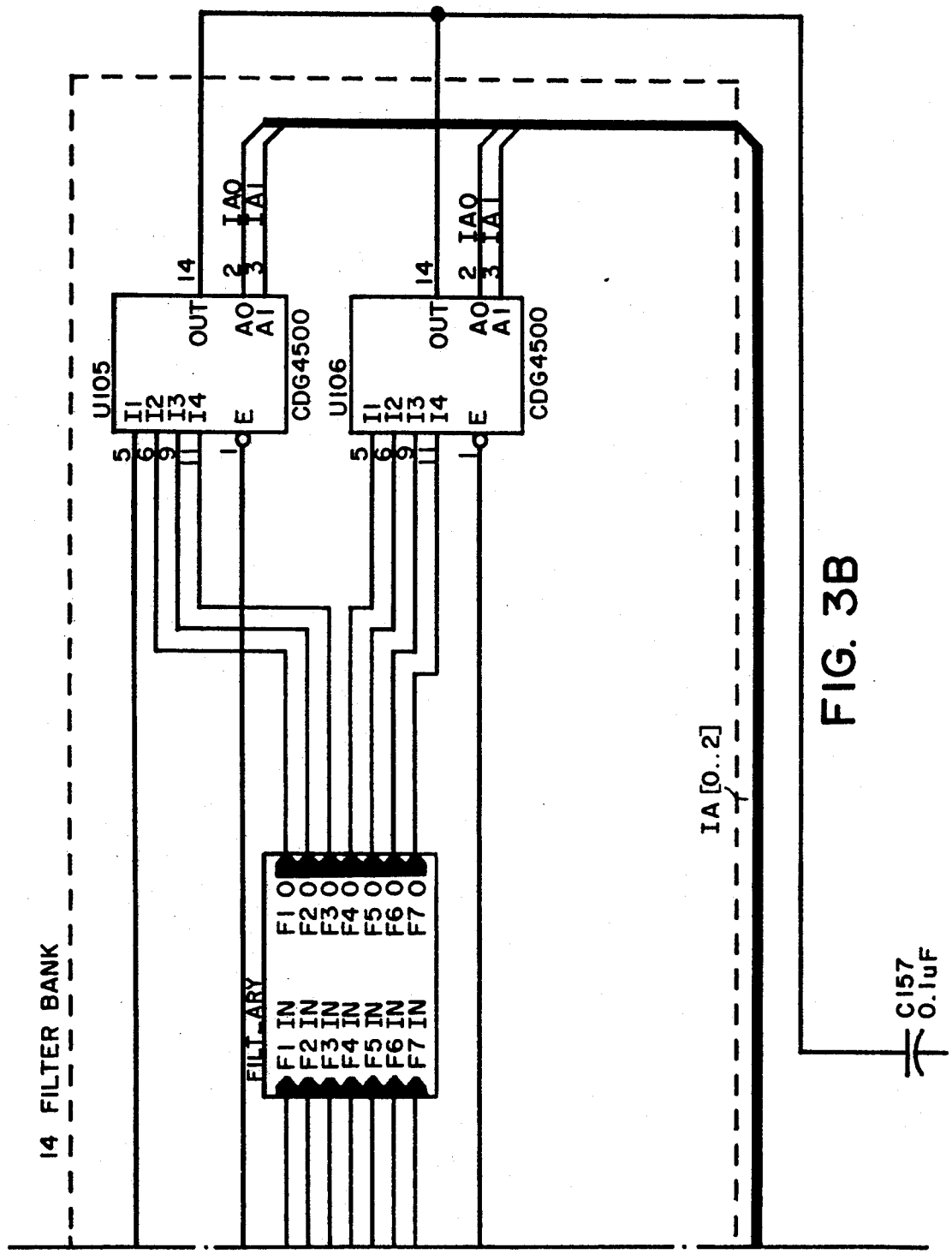
Figure 3C:
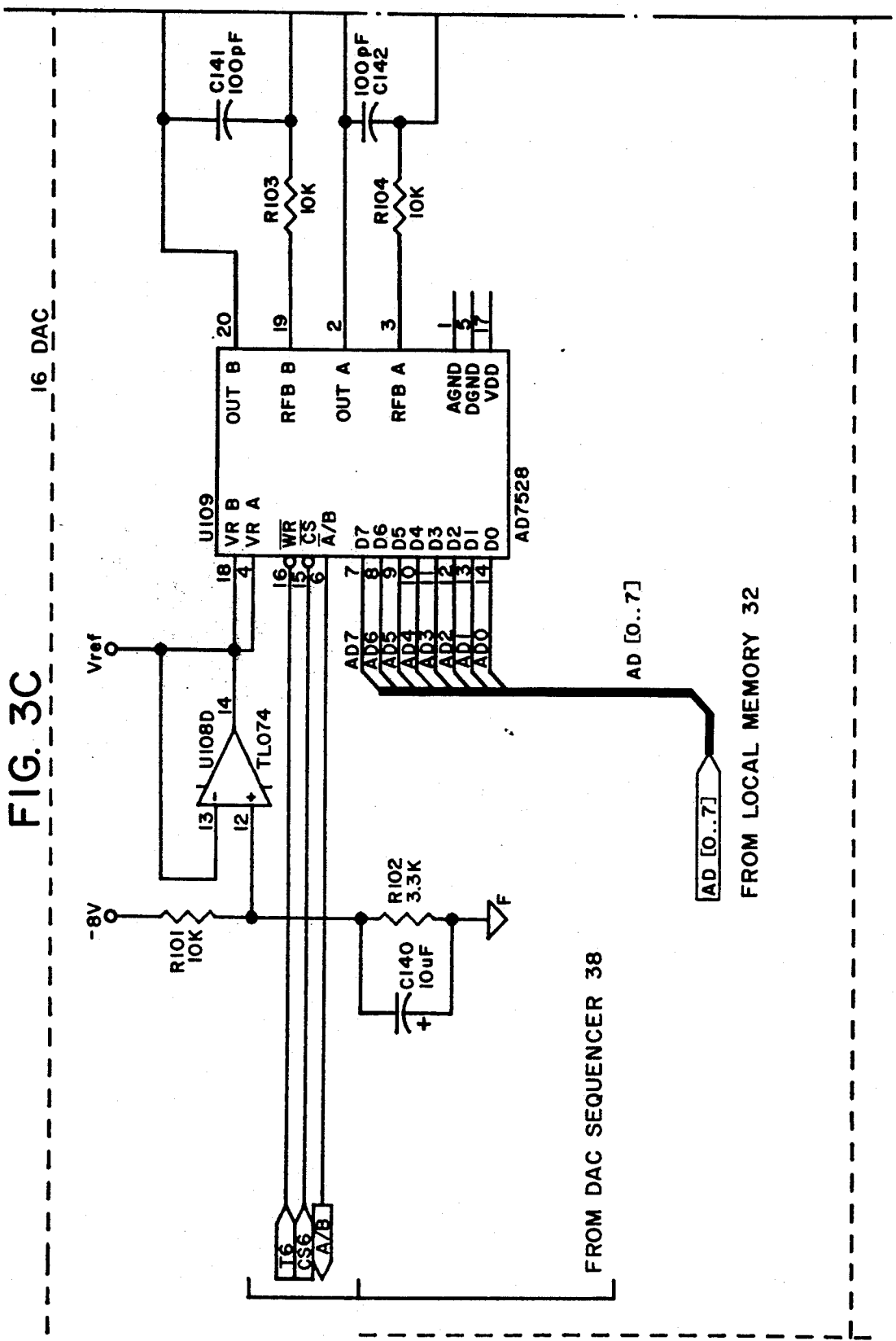
Figure 3D:
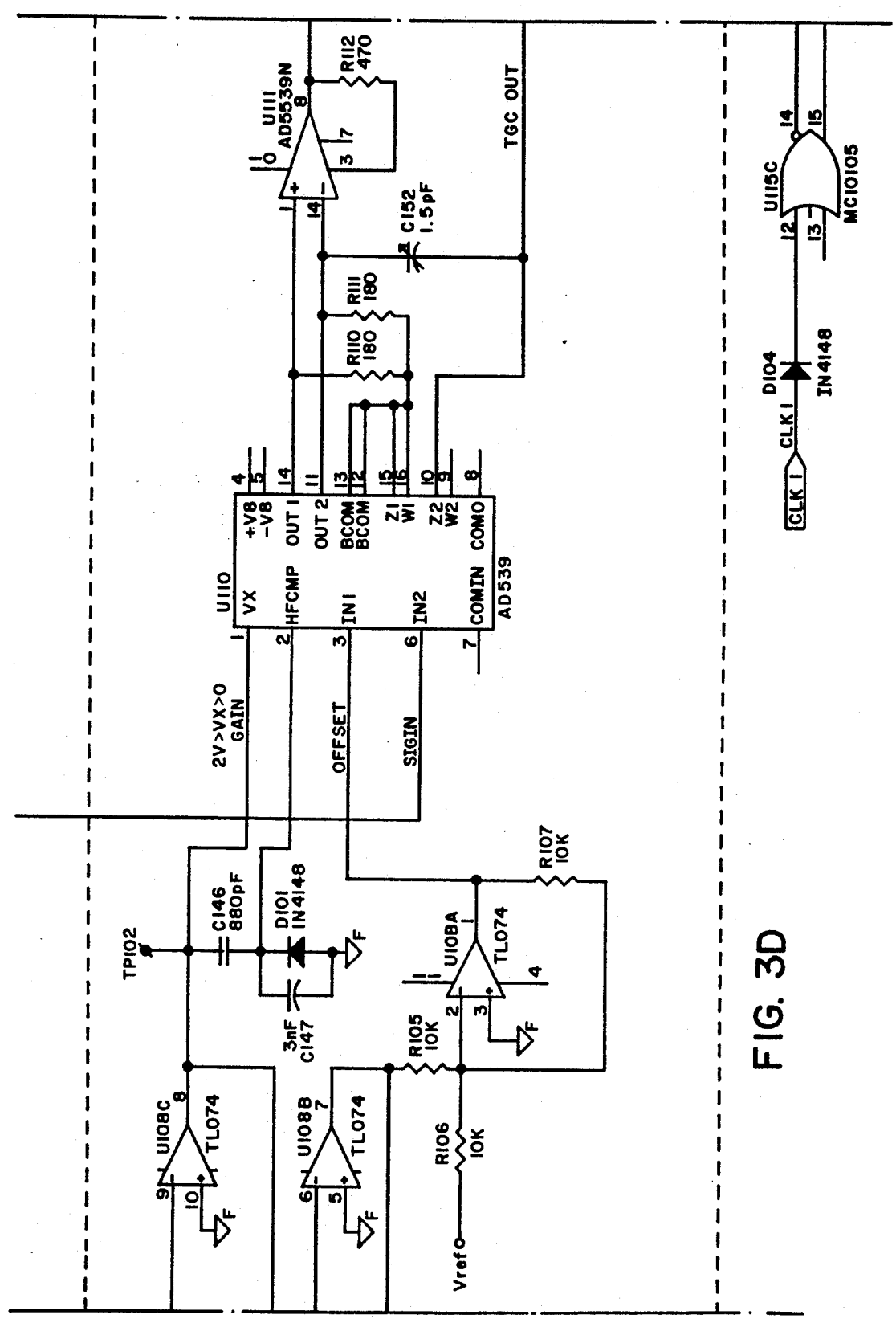
Figure 3E:
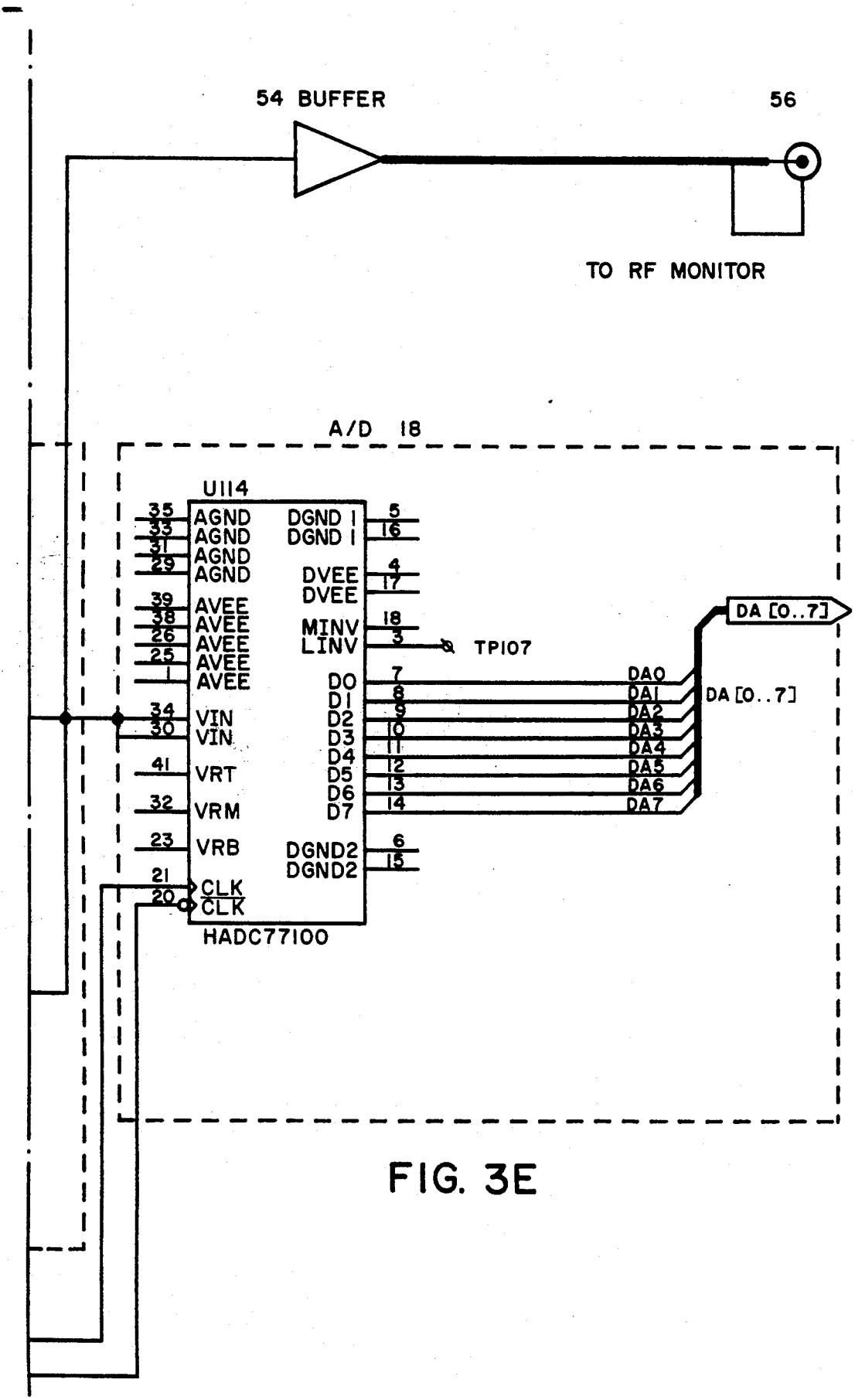
Figure 4:
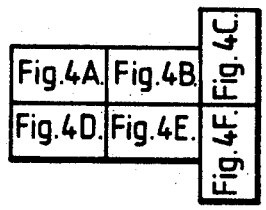
Figure 4C:
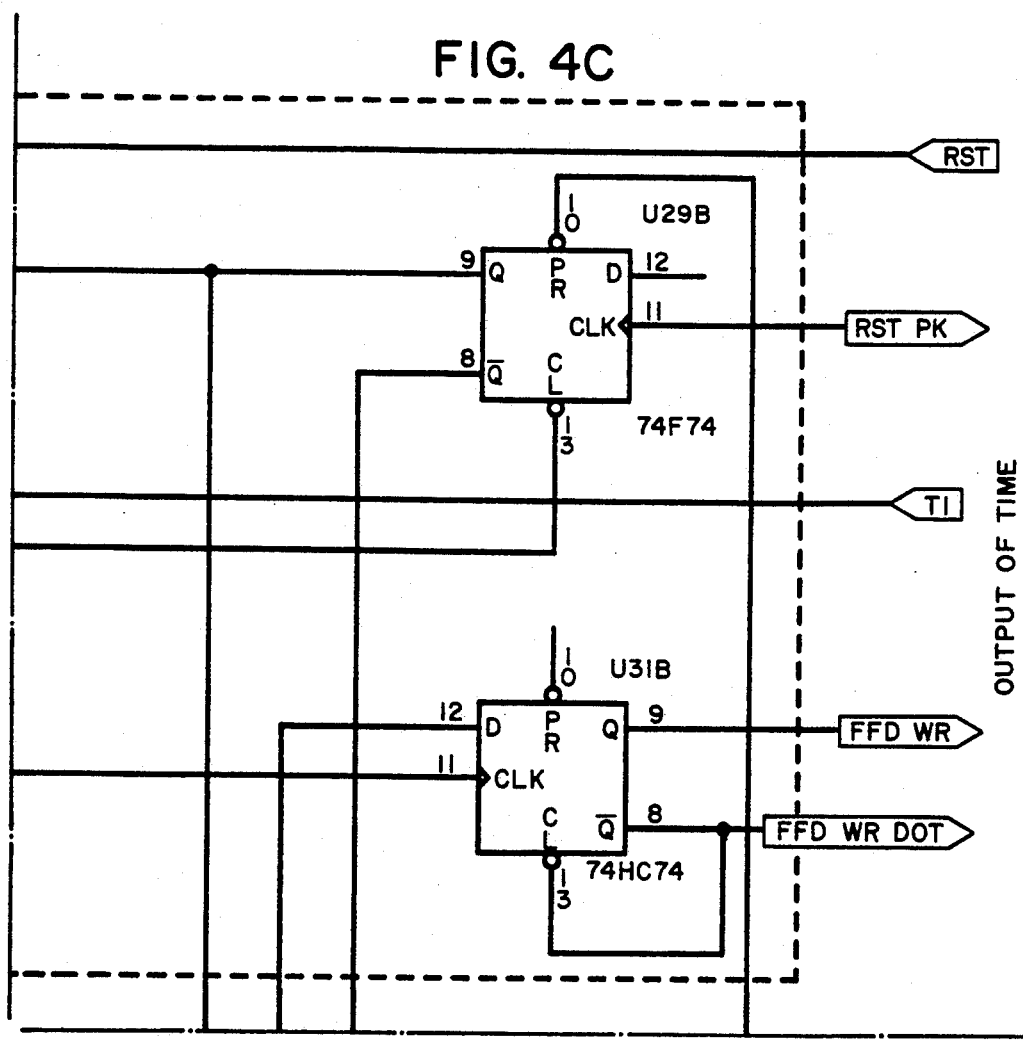
Figure 4B:
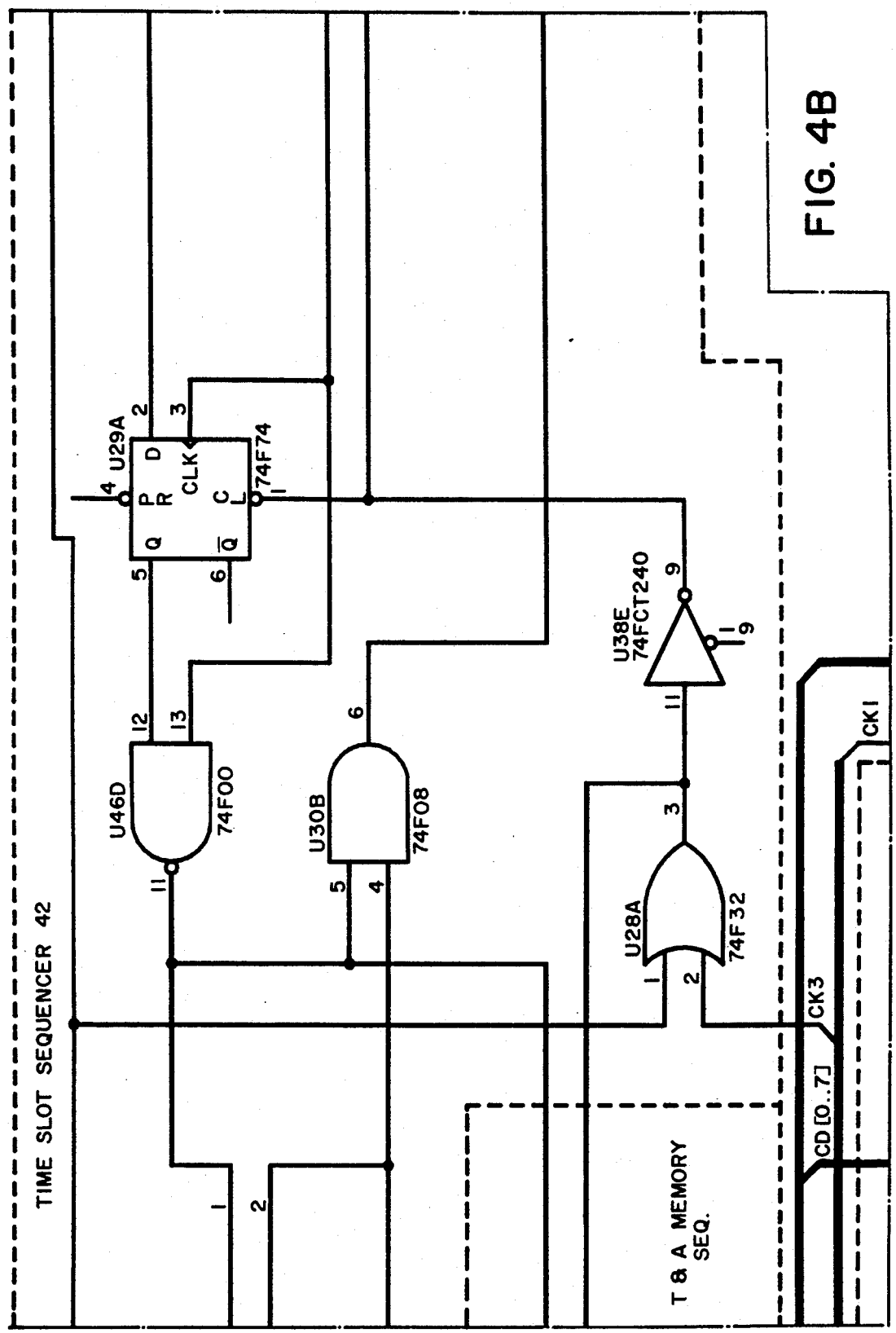
Figure 4D:
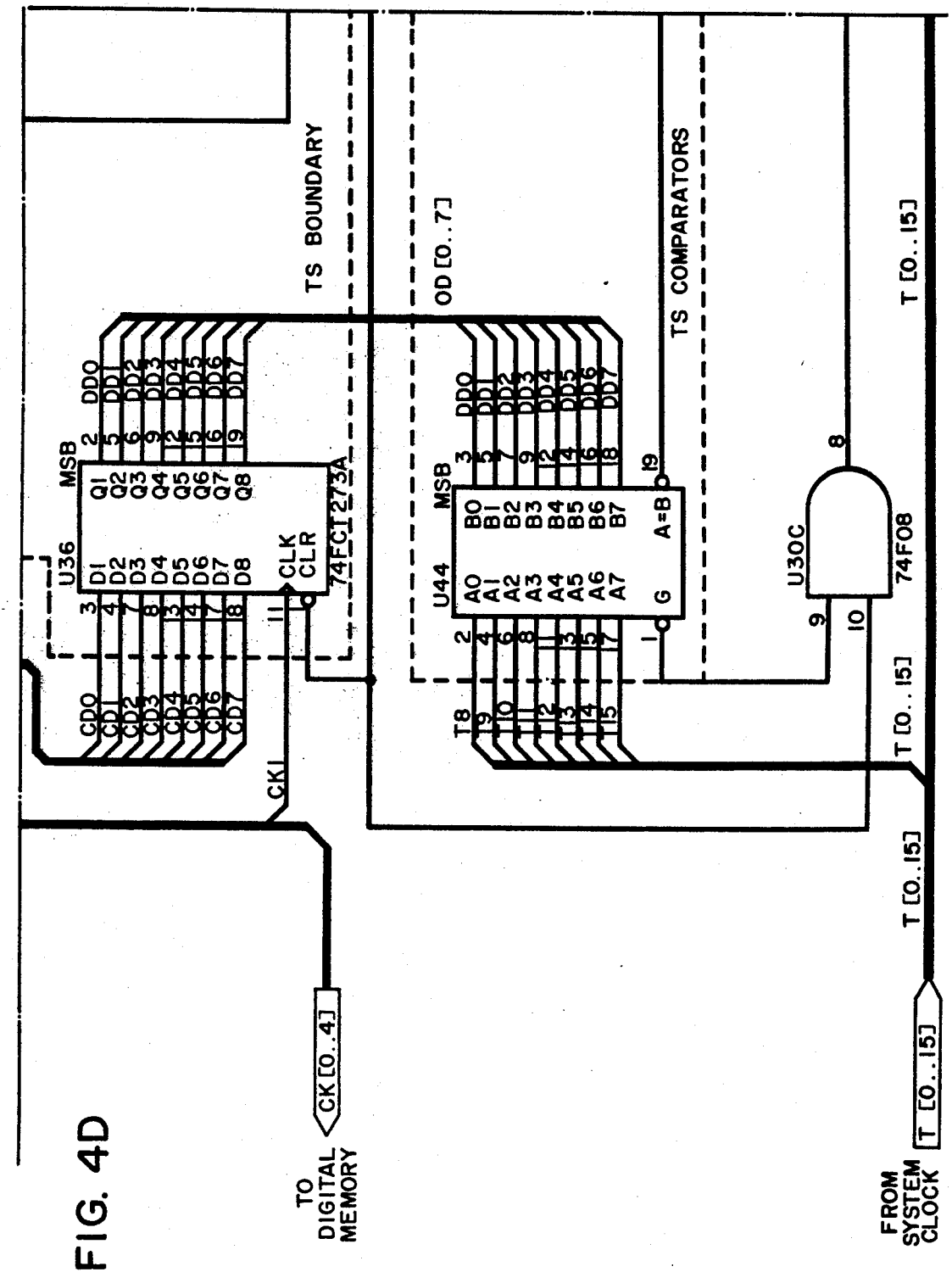
Figure 4E:
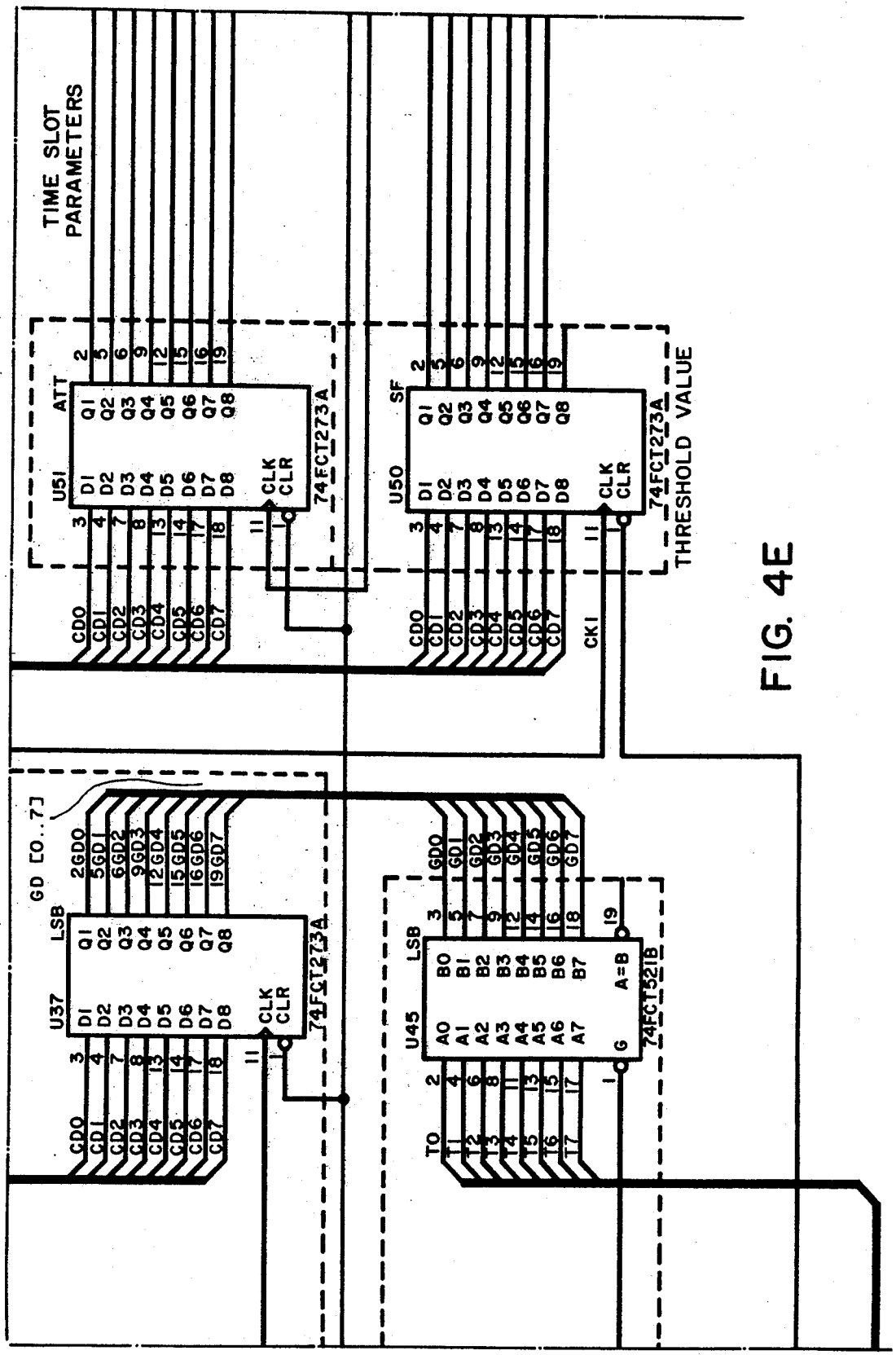
Figure 4F:
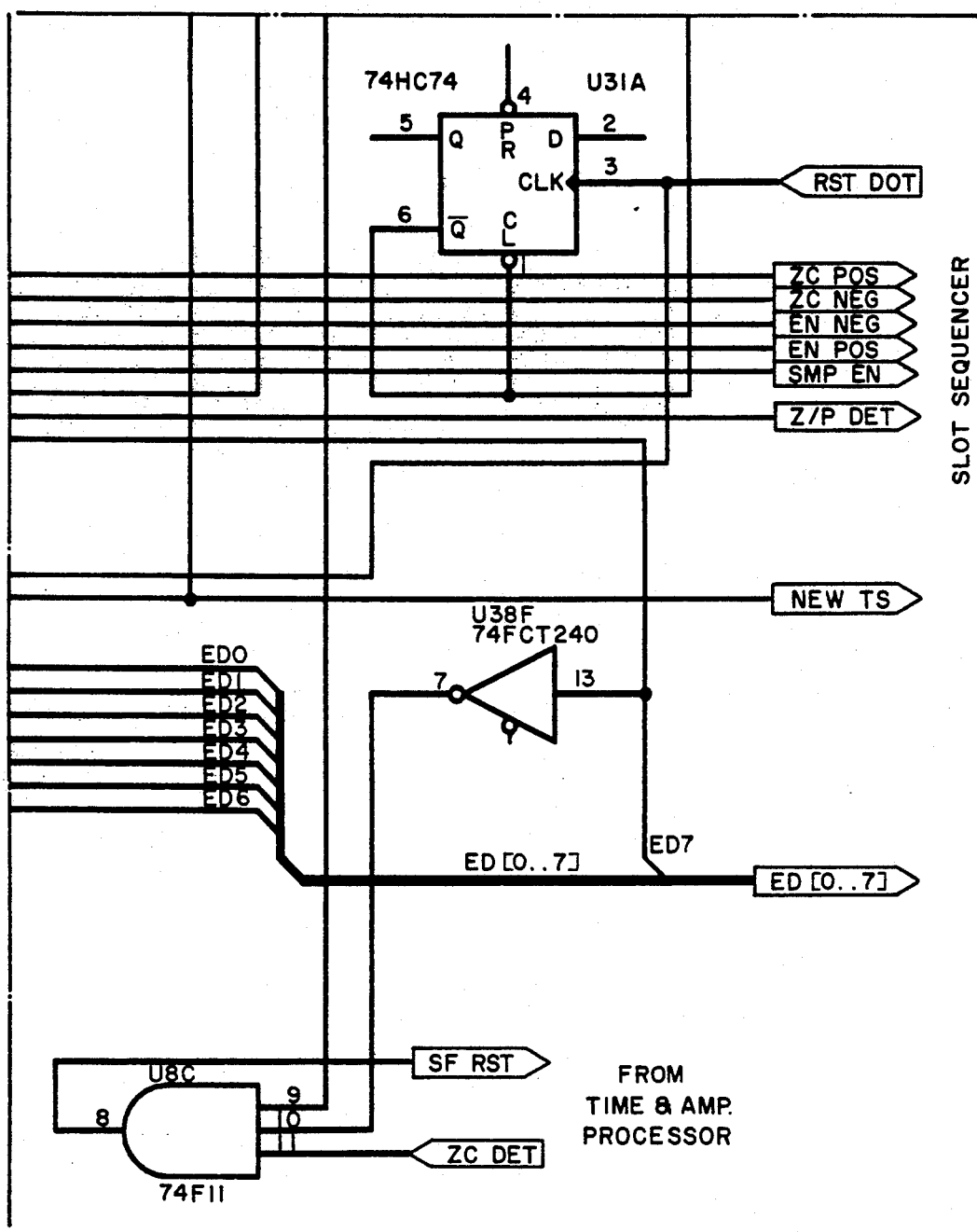
Figures 5, 5D:
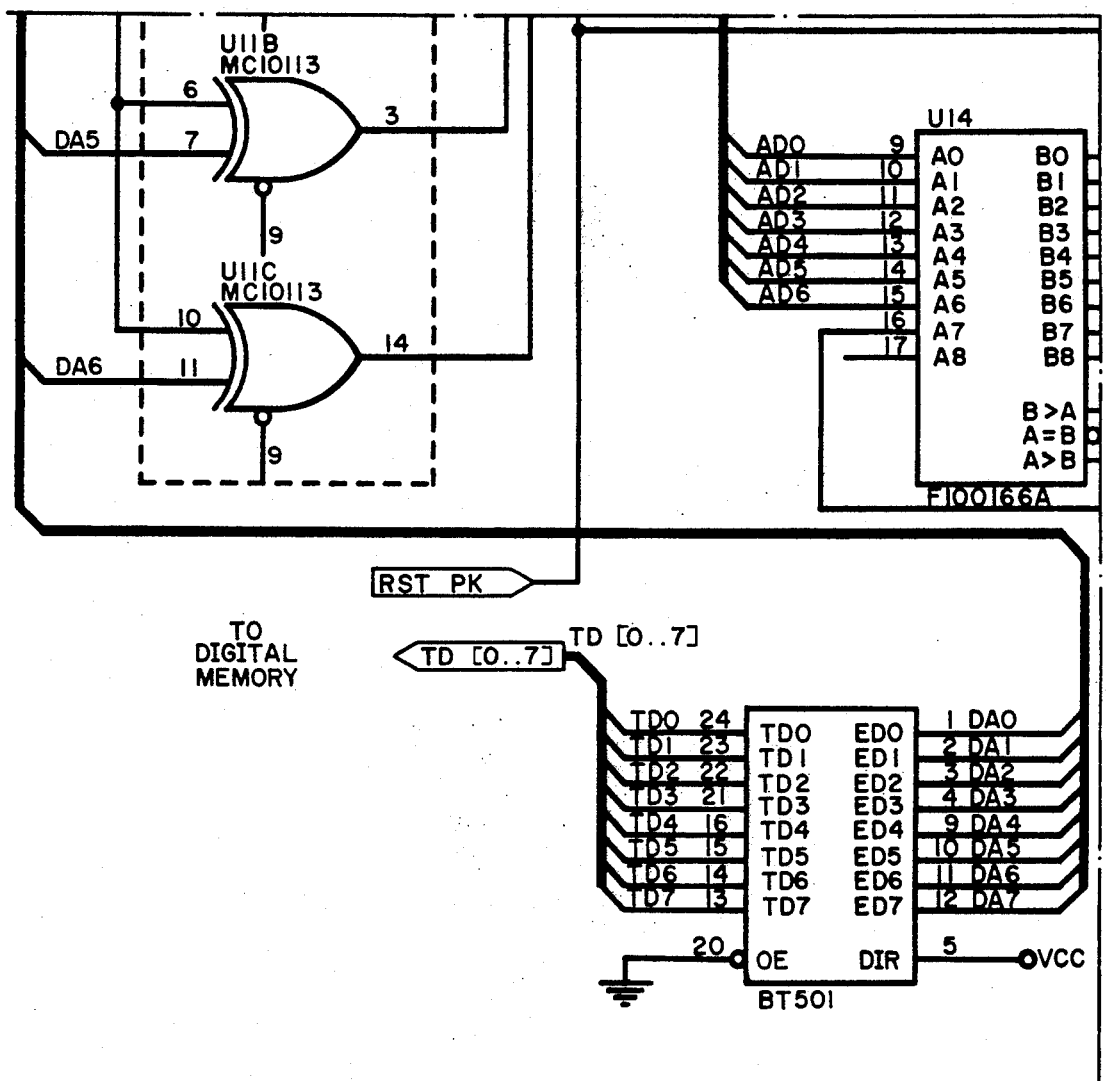
Figure 5A:
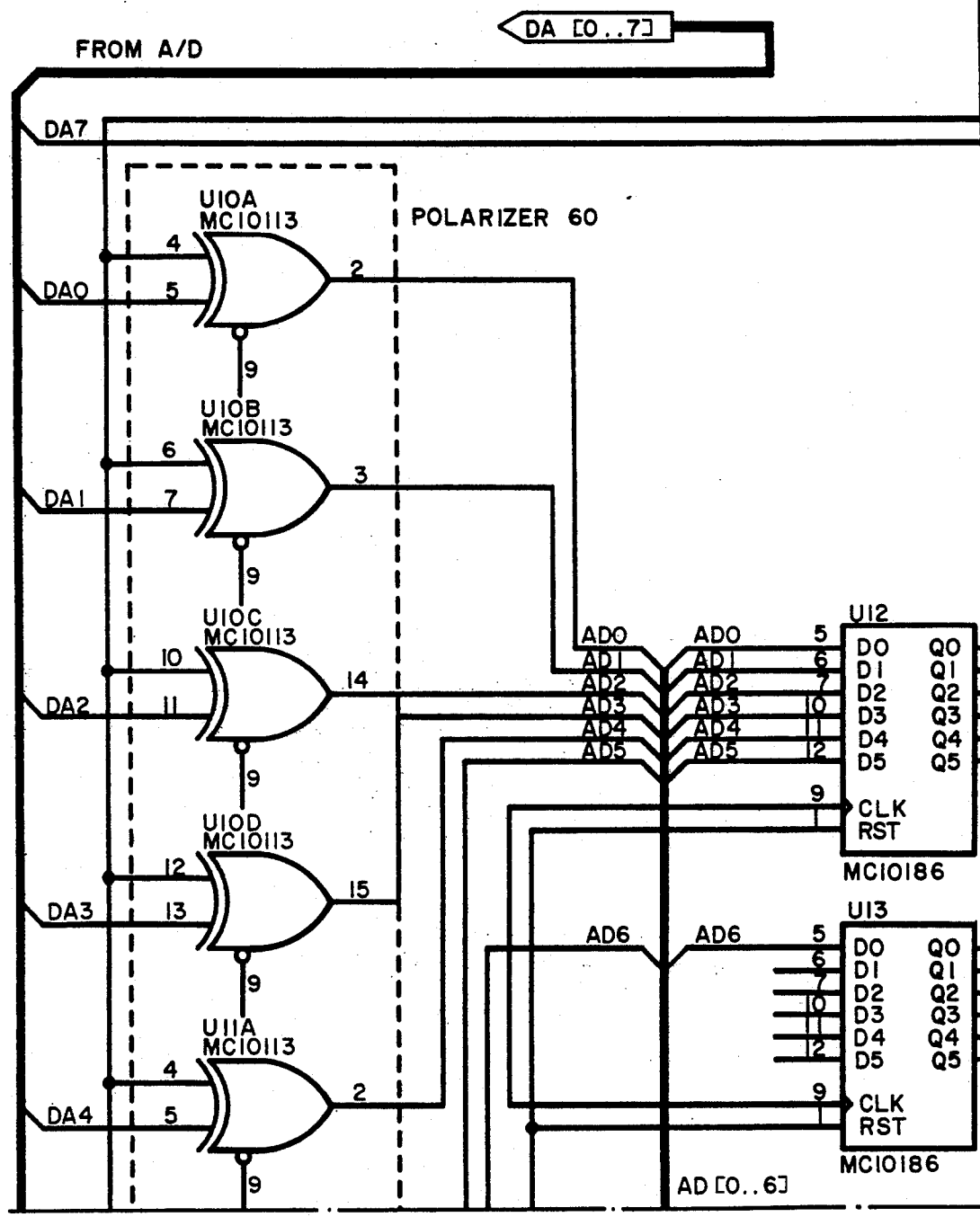
Figure 5B:
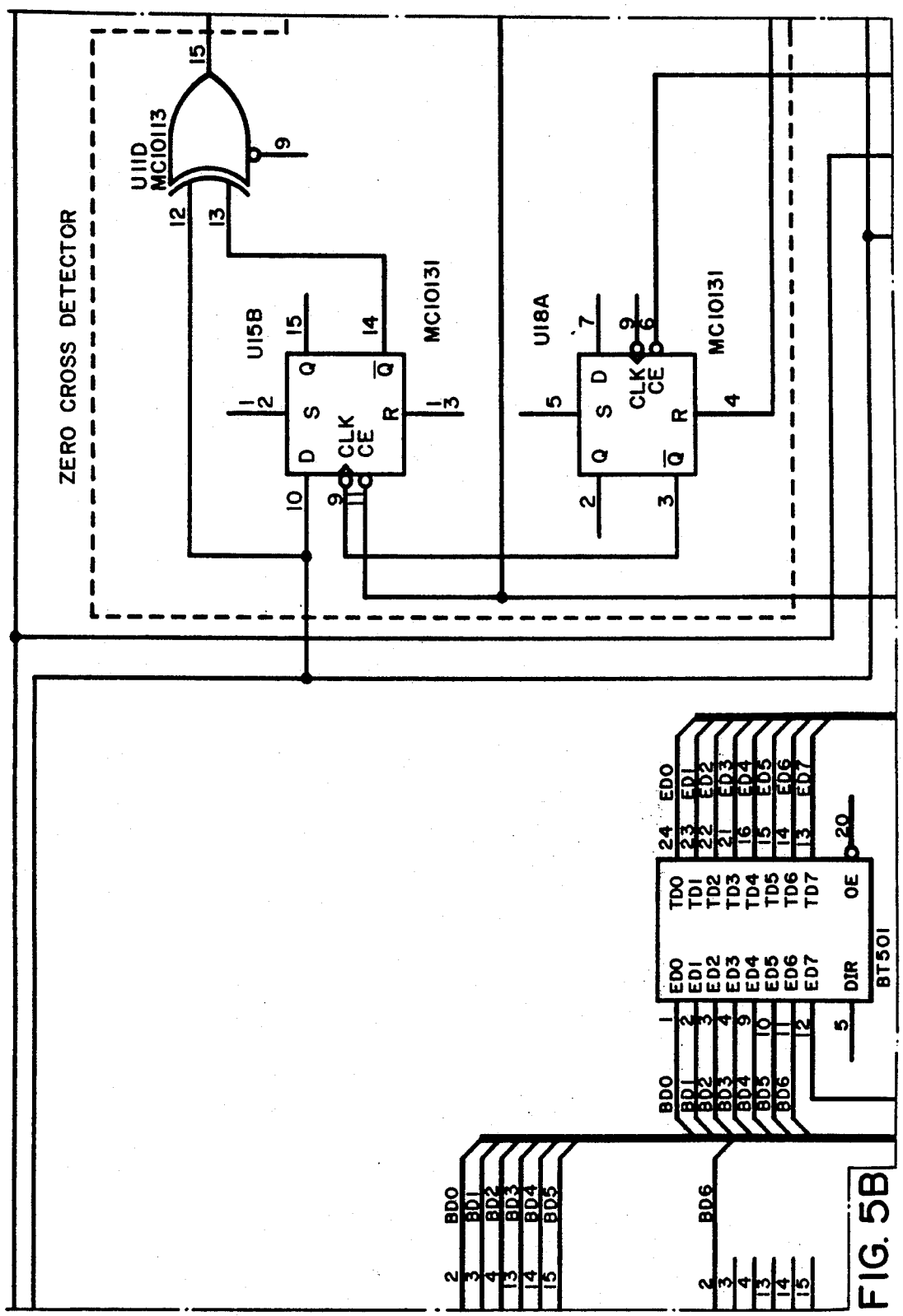
Figure 5C:
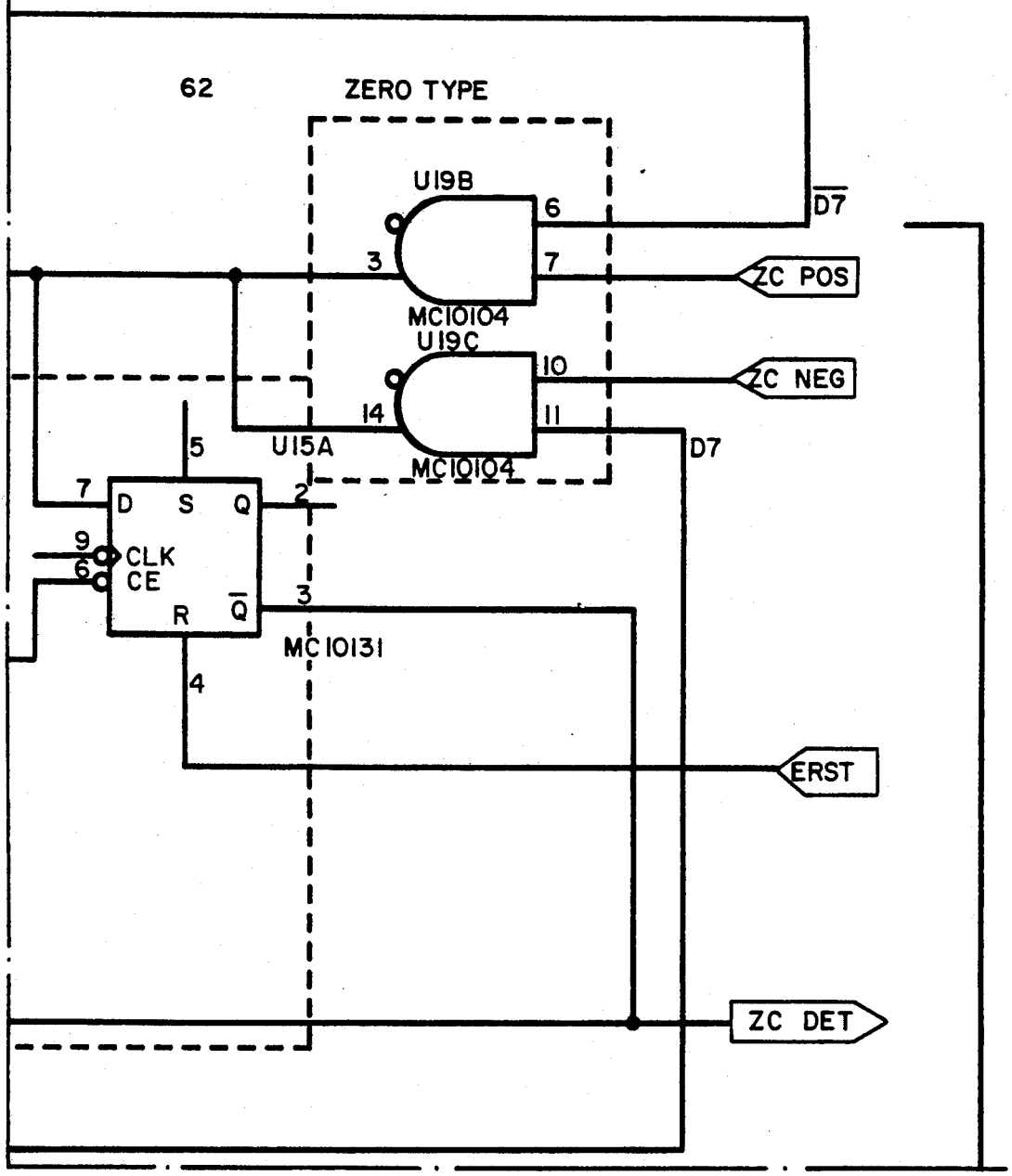
Figure 5F:
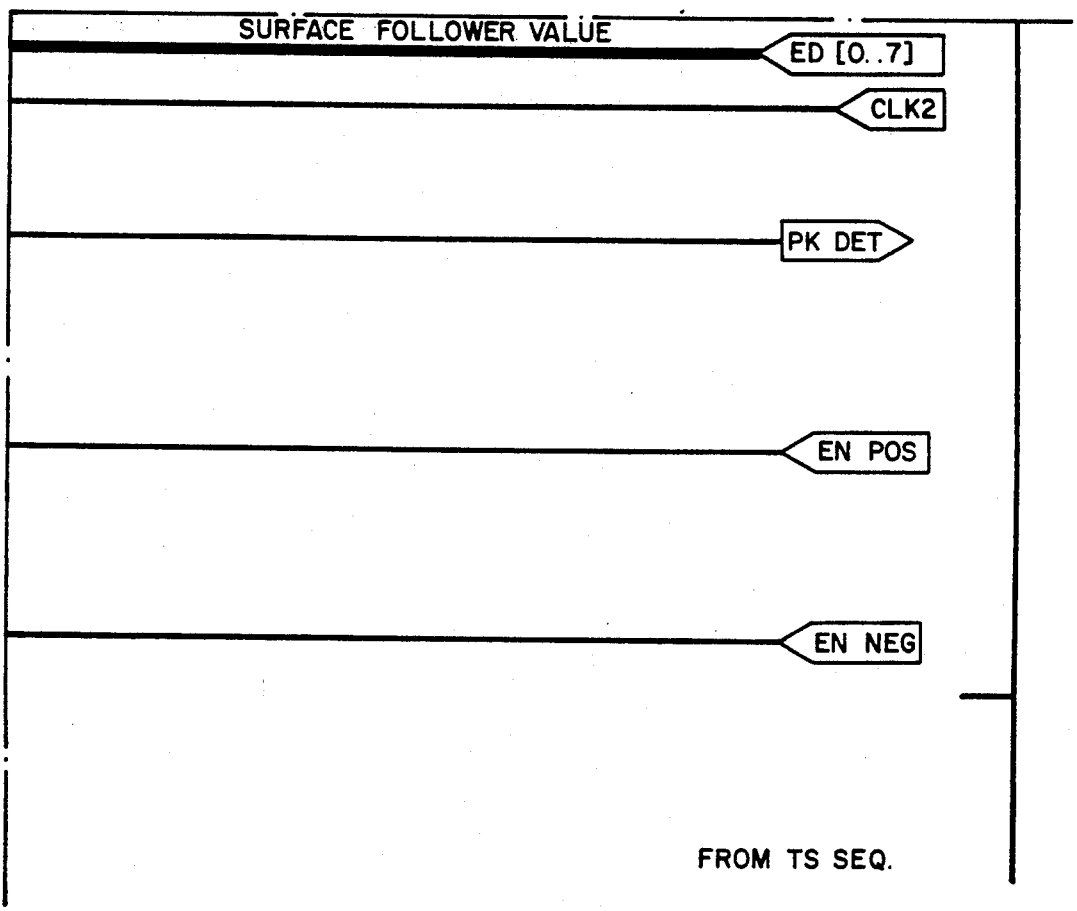
Figure 6A:
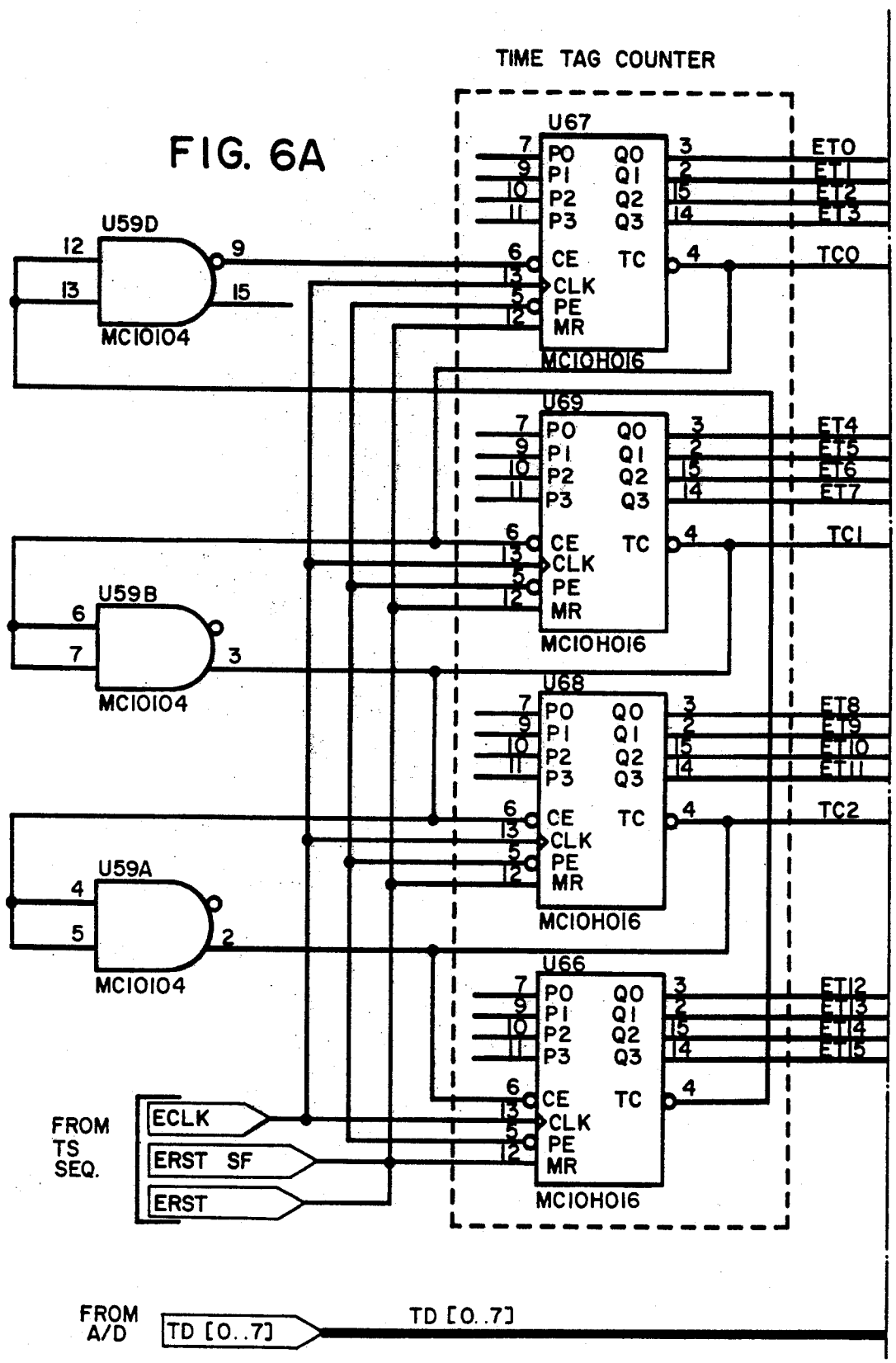
Figure 6C:
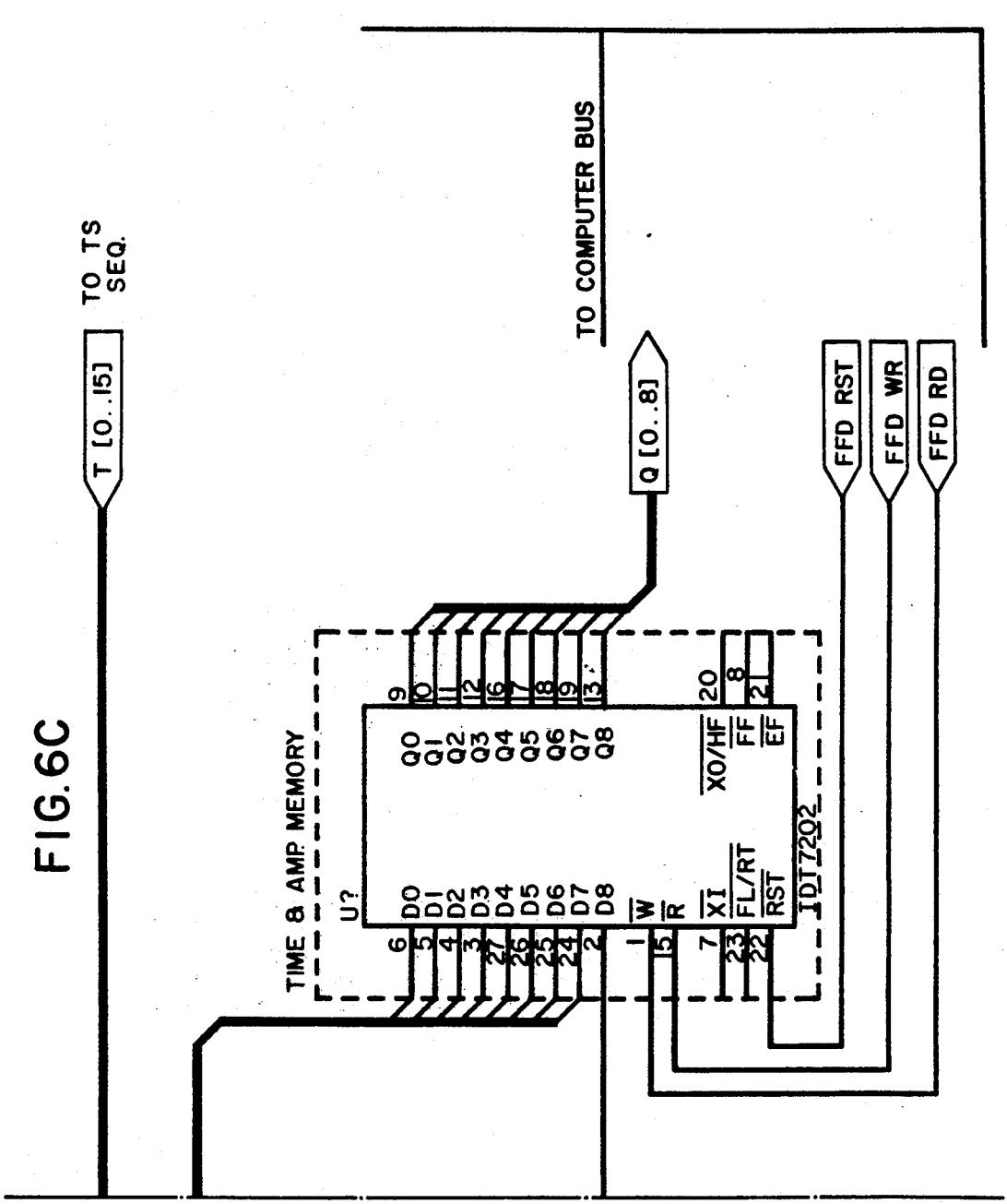
Figure 6D:
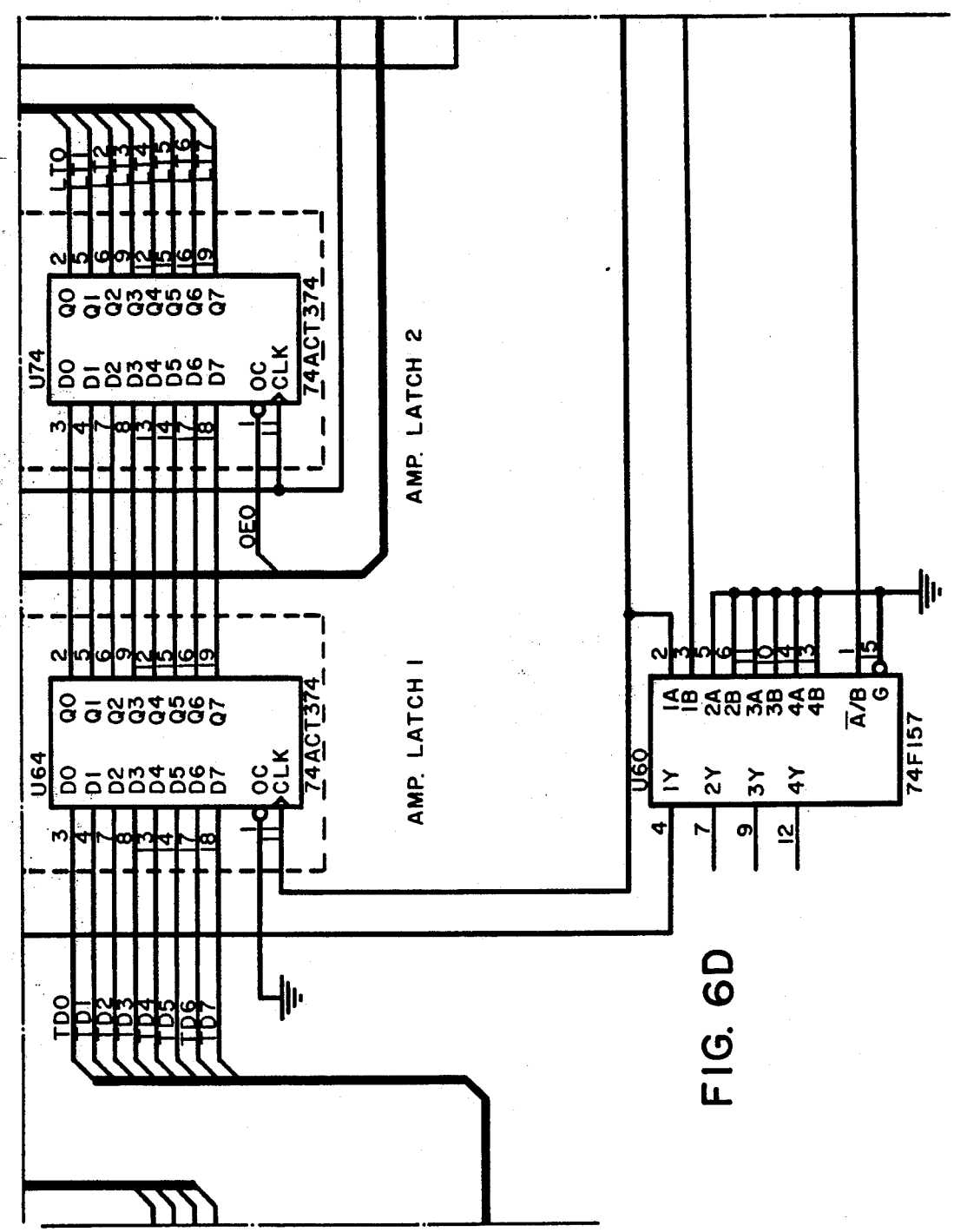

There is seen in FIG. 1 a plurality of separate, remote pulsers 2 and a corresponding number of preamplifiers 4, each pulse and preamplifier being connected to a probe (not shown) for generating excitation pulses, e.g., ultrasonic pulses, and receiving the resulting signals to be applied to the data acquisition and processing device 6. A separate pulser 2 and preamplifier 4 are required for each of the device input channels e.g., eight channels. The pulsers 2 are triggered by a pulser trigger generator 8 controlled by a master computer via a local memory 10. The latter is also operationally coupled to input selector 12, which is connectable to the preamplifiers 4 for receiving signals from the probes and selecting the desired channel, to the filter bank 14 and to a distance amplitude correction (DAC) and gates circuit 16. The setting of the filtering and of the distance amplitude correction can be effected for each channel independently. The output from the DAC and gates circuit 16 leads to a fast analog to digital A/D converter 18 for digitizing the conditioned signal. The sampling rate of the A/D is sufficient to sample the highest signal frequency expected, currently at 100 Million Samples per Second (MSS). This rate is suitable to process signals of up to some 20 MHz.

Following digitization the signal is processed in two parallel channels 20, 22. The channel 20 transfers the entire digital sequence to a sequential memory 24 for temporary storage. The second channel 22 first processes the signals in a time and amplitude processor 26 to identify the peak and zero-crossing points, and associates the signals with a Time Tag. The processed data is stored in a separate time and amplitude memory 28, for subsequent transfer to the computer bus 30.

The setup parameters which are stored in the local memory 10 include:
number of active input channels;
number of free-run pulser trigger cycles;
pulser synchronization mode (External/Internal);
pulser repetition rate;
filter type per channel;
DAC form per channel;
Offset per channel;
number of active Time-Slots and their position per channel;
Time Slot trigger (Normal/Surface follow) per channel;
peak type (positive/negative/absolute) per Time Slot;
Time tag initiator (peak/+ve slope zero-cross/−ve slope zero-cross/first zero-cross), per Time Slot;
full digital waveform enable per Time Slot, and digitization rate, global.

The operation of the device will now be described first with reference also to FIG. 2.

The data acquisition and processing of the present invention consists of four major sub-systems: system programming memory, pulser's trigger generator, analog signal preconditioning and digital data acquisition and processing. All of these sub-systems are controlled indirectly by the master computer which programs all the functions with the aid of the local memory. Both processed and raw data are stored for access by the slower computer bus asynchronously.

The system programming memory consisting of the local memory 10 receives and accepts all setup functions via the host computer bus 30. In the embodiment shown in FIG. 2, the setup functions are sent in coded form and stored in the local memories 32, 34 and 36. A local memory decoder serves to map the local memory 10 into the computer memory space. This facilitates rapid programming of setup parameters permitting the host computer to reprogram the device in real-time.

In another possible embodiment (not shown) the entire setup is stored and controlled by a microprocessor which receives high level instructions from the host. This processor then proceeds to initialize and set other functions of the device in a manner similar to that described above. The advantage of employing such a processor is improved operational flexibility in real-time.

The pace of the major functions of the device, which are: channel selection, DAC time base generation, digitization rate, Time Slot management, signal Time Tag base, and memory control are automatically controlled by sequencers 38, 40, 42 and 44 which, in turn, are clocked by a central timing module including a system clock 46 and clock selector 48 providing the basic synchronization of the system.

The trigger 8 generates triggering pulses to initiate the remote pulsers 2. The number of active pulser channels and the pulse repetition rate are programmed in local memory 32 by the host computer. The number of active channels stored in local memory 32 addresses a decoder (not shown) which is triggered by a cycle start pulse. The cycle start signal is activated by the channel sequencer 40. This setup ensures that only triggers for the active channels are generated in the trigger generator 8 in cyclic succession, to be applied to one or more of the pulsers 2.

The analog preconditioning circuit of the incoming signals from the probes includes the multiplexer 50, selecting the input active channel or channels, the filter bank 14 and the DAC and gating 16, for eliminating irrelevant echoes of the data. Gating may be effected by a channel sequence counter controlling the pulse repetition rate of each channel.

The incentive for using the channel sequencer 40 is the saving in expensive components of the circuit. This operation mode permits a number of channels to use the same high performance hardware through time-division multiplexing. Naturally, similar apparatus with multiple digitization and processing channels used simultaneously, can be envisaged for other applications.

The channel sequencer 40 drives the filter bank 14 and DAC and gates 16. These functions are cycled between channels, switching repeatedly to ensure that each channel is provided with its particular filter and DAC setting irrespective of the other channel settings. In other words, the filters and DAC profiles are reset before the initialization of each channel. The actual setting of the filters and DAC profile is stored in local memory 32.

The channel sequencer 40 may employ analog switches for transferring the signals. Alternatively, the selector may employ a circulator or a relay array. The number of active channels is determined in the channel sequencer 40 according to values programmed in local memory 32.

Any one of the different filters from the filter bank 14 can be selected for use with each of the input channels. The filters are switched in and out according to the selection of each channel, using a pair of analog switches driven by the filter address stored in the local memory. Other manners of filtration can be envisaged, including separate filter banks and active filter parameter control, a circulator, or a relay bank.

Referring now also to FIGS. 3 to 6, the DAC 16 is advantageously embodied by an analog multiplier in the form of a mixer U110 (FIG. 3). The input signal is multiplied by a reference voltage, which itself is generated by a D/A converter U109. The value of the D/A is determined and continuously updated by a vector sequence stored in local memory 32 and fed to the D/A converter synchronously with the main DAC clock generated by the DAC Sequencer 38. The DAC clock itself is produced through a separate oscillator, which is synchronized with the initialization of each channel or the surface follower signal. The sequence of numbers specifying the gain of the channel as a function of time, serves to compensate for material attenuation as a function of distance.

The gating of the channels is accomplished by the switching between channels according to the program in a programmable timer (not shown).

For continuous monitoring of the signal, an analog output of the preconditioned channel signals is output through an amplifier 52 and via a suitable buffer 54, to drive an RF monitor 56 such as a multi-channel oscilloscope. This output provides for continuous display of the signal in each channel for reference during the scan.

Digitization is performed by a fast flash A/D converter 18 (UI14 in FIG. 3). The digitization rate is determined by the programmable timer, which is set up by means of a setup store latch, itself loaded directly from local memory 32.

Following digitization the signal is routed in the two paths 20 and 22. Full digital sample storage is routed to memory 24 and to the time and amplitude processor 26. The actual information to be stored in each Time Slot is determined by the desire setup in each Time Slot. This setup can range from full wave digitization, to Time Slot peak and Time Tag detection. Peak and time can be selected from a number of possibilities: positive, negative or absolute value peak, and time of peak or time of zero-crossing following the peak.

An important feature of the device is the Time Slot sequencer 42 (FIG. 2). It is responsible for generating the Time Slot start and stop signals which are used to operate the entire digital part of the device. The preprogrammed Time Slot boundaries are loaded into the boundary latches (U36 and U37 in FIG. 4). The first boundary (the start of Time Slot 0) is loaded on system cycle reset signal. These values are compared to the systems clock 46 counter by means of the digital comparators U44 and U45, which generate a boundary signal when the system time is matched to that of the preprogrammed boundary. This signal also loads the next boundary value from the local memory 34 (U26 in FIG. 4) to the boundary latches. The Time Slot settings peak type, zero-crossing type, digitize enable, and surface follower enable, are loaded simultaneously to the Time Slot parameters latch U51. Similarly, the value of the surface follower threshold is loaded into latch threshold U50. This value serves to define surface follower threshold if it is enabled. The latch SET and RESET sequence of these modules is controlled by the Time Slot sequencer 42, comprising four flip-flops U29A, U29B, U31A, U31B and several logical gates U30A, U30B, U46D, U28A.

The digital memory 58 is activated on request of full digital information for a specific Time Slot. Data is transferred to memory 36, which serves as a buffer to allow the slower computer bus sufficient time to read the data. Data rates at this point are very high (exceeding 100 MHz) and require a very fast memory. If the memory speed is limited, a serial to parallel data converter can be used to accommodate the high sample data rate. Such a converter routes the data to several different memories, say n, in cyclic succession: the first data word is transferred to a first memory, the second to a second memory, etc. The resulting data rate in each of the output branches is therefore reduced n-fold. Other serial to parallel conversion methods include bit-wise shift registers with bit descrambling.

The time and amplitude processor 26 detects the peak in each Time Slot and assigns this peak with a Time Tag. This circuit is shown in detail in FIG. 5. The digitized data is first polarized in a polarizer 60 to accommodate the different peak polarities desired (positive, negative, or absolute). This is performed by an array of XOR gates (U10A through U10D and U11A to U11C) which invert the bits of a negative signal if a negative peak is requested. If absolute peaks are requested, the signal is inverted by U19A and U19B only when the signal is negative. A digital comparator U14 compares the incoming data with the previous maximal signal value, which is stored in a latch U12 and U13. If the current signal is found to exceed the previous maximum, the latch is loaded with the current value, which now serves as reference. The entire module is reset on initiation of each new Time Slot so that the peak value of the specific Time Slot is eventually found in the latch as the Time Slot terminates. This value is simultaneously transferred to the double latch system in the time and amplitude memory 28. A pulse signifying the detection of a peak is simultaneously generated and applied to the time and amplitude memory 28, requesting a Time Tag for the peak.

One exception to this operation mode is found when the Time Slot is programmed to commence at the detection of the surface echo. This mode is called surface follower. In Time Slots that have been so programmed, the peak detection comparator U14 is loaded with the surface follower threshold value, rather than the previous peak value. This threshold is set to ensure that erroneous triggering by threshold triggers the Time Slot. In this operational mode the activation of the identification of a value greater than the preset threshold resets the system, defining the start of the Time Slot in question. Surface follower mode can be defined for any Time Slot, and is not restricted to the first one, as is common. This is a useful feature for tracking signals that occur after the surface signal.

The Time Tag of the zero-cross following a peak is effected in the zero-cross detection module 62. Identification of the time slot peak SETs the peak flip-flop U18A. This conditions the zero-cross flip-flop U15B which is then SET on identification or a zero level transition in the signal. Such an arrangement ensures that the first zero following a peak is detected. The zero-cross is heralded to the time and amplitude memory 28 to request a Time Tag for the zero cross.

Zero-cross detection also allows the selection of three different zero-cross types: zero-cross on negative, positive or either signal slopes. This feature is necessary for accurate timing applications where signal inversion is expected, and the timing must be limited to a prespecified signal slope. The zero-cross is accomplished with the two AND gates U19B, U19C which filter the correct zero cross generated by the flip-flop arrangement, in accordance with the settings read from local memory 34.

The time and amplitude memory 28 (FIG. 6) includes a current peak latch U64, which serves to capture the current peak data continuously as it is updated during the Time Slot. Immediately on termination of a Time-Slot, this value is transferred to a second latch freeing the current latch to continue updating the peak of the new Time-Slot. This value is subsequently transferred to the time and amplitude memory buffer U74 (FIG. 6) to allow readout by the host computer at slower rates. Other memory types are also appropriate.

A similar double latch arrangement (U62, U72 and U63, U72) is used to transfer the Time Tag of the peak (or zero-cross as programmed). The time value is read off directly from a 16 bit time counter U66, U67, U68, U69 to be loaded into the current time latch (U62, U72) on the occurrence of the preprogrammed Time Tag event (peak or zero-cross). This data is also entered in a memory buffer (U63, U72).

A channel change marker generated by U61 serves to signal the change in channel recorded data.

The Digital Signal Processor (DSP) 64 in FIG. 2 is optional. This module enables processing of the data collected in real time. It improves the performance of the overall system in freeing processing tasks from the host computer. The DSP 64 has access to both the digital memory 58 and the time and amplitude memory 28 to draw data for processing. The processing procedures are stored in its own local memory 36 and the procedure results are transferred to the DSP memory/buffer 66. Further typical applications which could be processed include Fourier analysis, Deconvolution, and other signal reconstructive algorithms.

The invention will now be further illustrated with regard to the two examples shown in FIGS. 7 and 8.

EXAMPLE I

Detection of Bonding

Figure 7A:
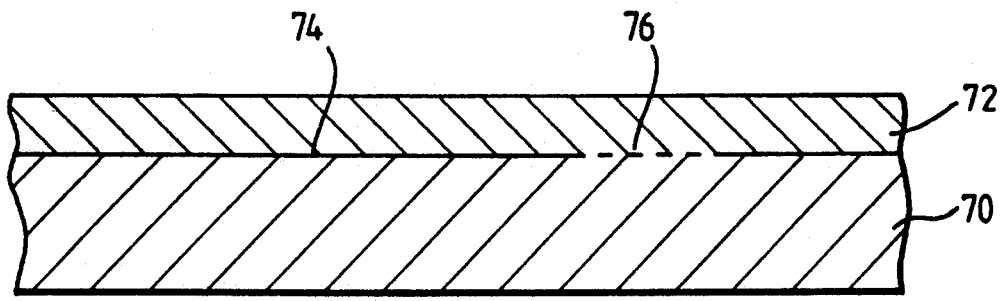
FIG. 7a is a cross-sectional view of a piece of a liner bonded to a piece of metal.
Figure 7B:
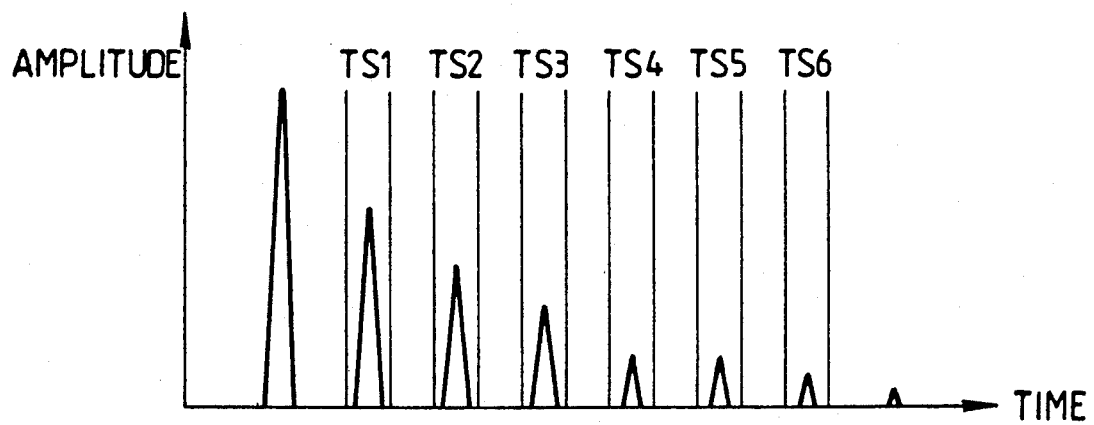
FIG. 7b is a characteristic time-amplitude representation illustrating reflected PEs of an acceptable bond area.
Figure 7C:
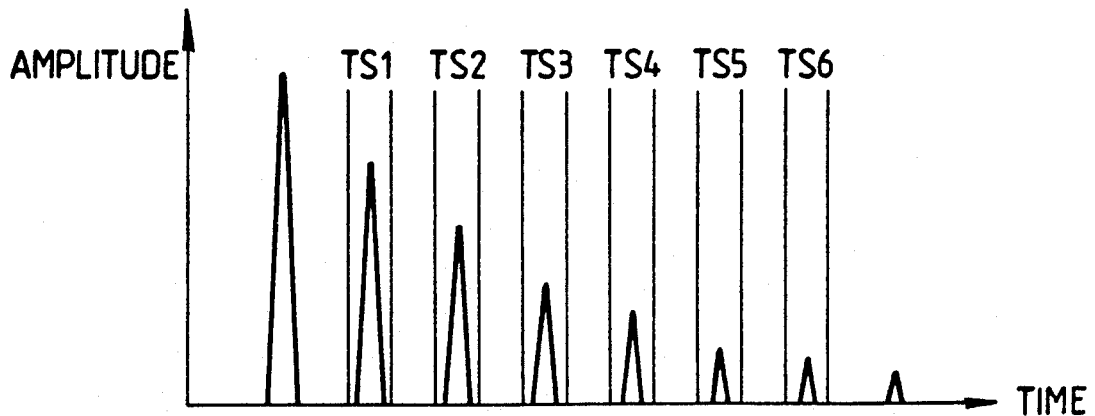
FIG. 7c is a characteristic time-amplitude representation illustrating reflected PEs in an area where bonding is not completed.
Figure 8A:
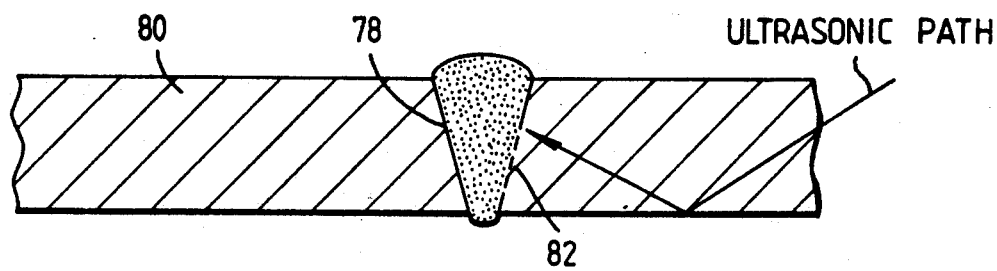
FIG. 8a is a cross-sectional view of a metal to metal weld area.

In this example it is required to inspect a metal 70 to liner 72 bond as shown in the cross-sectional view of FIG. 7a. Typically the liner 72 is made of highly absorbing material and no echo is expected from its backwall. The rate of decay of successive echoes from the backwall of the metal/liner interface indicates the bonding degree between the two materials. The reflected signals from a bonded interface 74 and an unbonded interface 76 are shown in the rectified wave traces of FIGS. 7b and 7c, respectively. It is found that greater attenuation of the successive reflections occurs when the bond is tight (FIG. 7b), since more of the signals are absorbed in the liner 72.

In a standard, commonly used, two gate system, it would be necessary to rely on comparative peak amplitude measurement of two of the reflected pulses. Since the signal is typically very unstable in such applications, interface bonding resolution would be limited, as would be the reliability of the inspection. The latter are considerably improved by using the e.g., six Time Slot setup (TS1 to TS6) shown in FIGS. 7b and 7c. The peak in each Time Slot is obtained for generating a more accurate measure of the bonding strength by averaging and extrapolation operations. Scan speed and resulting analysis, are thereby not reduced.

EXAMPLE II

Distinction Between Crack and Porosity in Weld Seams

Figure 8B:
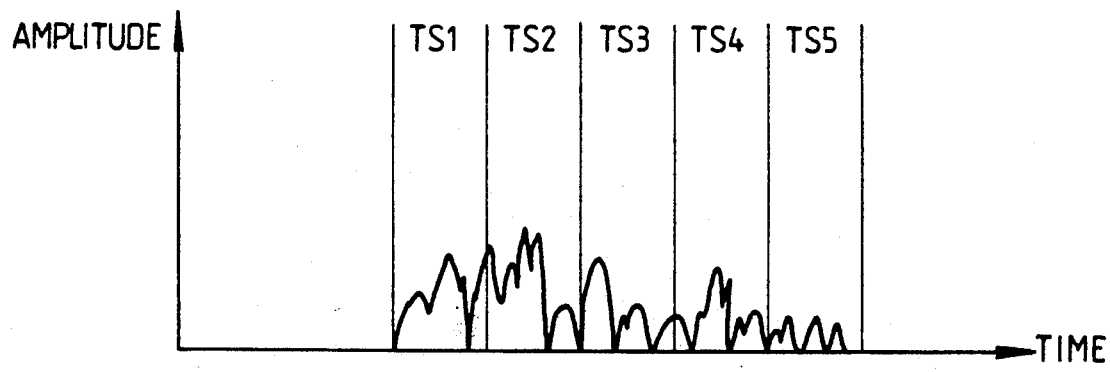
FIG. 8b is a time-amplitude graph of a PE signal from an area of an acceptable weld.
Figure 8C:
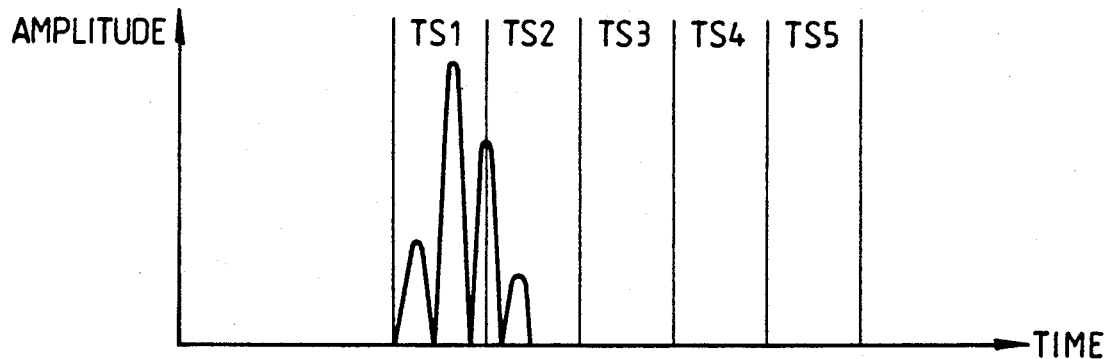
FIG. 8c is a time-amplitude graph of a PE signal from a crack in a welded area.

In inspecting welded seams 78 in a metal 80 (FIG. 8a), it is important to discriminate between weld porosity and weld-border cracks 82. The two defect types produce different signatures. FIGS. 8b and 8c indicated typical results for porosity and cracks, respectively.

The e.g., five Time Slot setup (TS1 to TS5) shown in FIGS. 8b and 8c illustrates the manner in which the detection of the peaks in these Time Slots can provide indication of the presence of a flaw, namely, large reflection levels (FIG. 8c) in any of the Slots. At the same time, it is possible to discriminate between cracks, with large variance between the five Time Slot peaks and porosity, where detected peak variance is small.

It will be evident to those skilled in the art that the invention is not limited to the details of the foregoing illustrative embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. In a programmable receiver for detecting signals reflected from, or transmitted through, a material for analyzing flaws in said material, the improvement comprising:
   an analog to digital converter for receiving signals from said material and converting the received signals into digital form; and
   a memory and a processor connected in parallel for receiving signals from said analog to digital converter, said processor comprising circuit means for dividing said signals into a multiplicity of separate, independent sections for selective evaluation of waveform portions as contained in each of said sections.

2. The receiver as claimed in claim 1, wherein said circuit means of said processor is further operative for detecting peak signal amplitudes within one or more of said sections.

3. The receiver as claimed in claim 1, wherein said circuit means for dividing said signals into a multiplicity of separate independent sections for selective evaluation of waveform portions comprises means for assigning a time value to a peak, or to a time associated with a zero-crossing following a peak, of a signal in each of said sections subjected to said selective evaluation.

4. The receiver as claimed in claim 1, further comprising a time and amplitude memory connected to said time and amplitude processor, for storing data processed in said processor and for subsequent transfer to an additional processing device.

5. The receiver as claimed in claim 1, further comprising a multi-channel signal transmitting and receiving means for transmitting excitation pulses to said material being analyzed and for receiving resulting signals from said material being analyzed, the signals received from said material by said multi-channel signal transmitting and receiving means being sent to said analog to digital converter.

6. The receiver as claimed in claim 5, where the multi-channel signal transmitting and receiving means comprises a trigger circuit connectable to at least one pulser leading to a corresponding number of probes for transmitting to a material and receiving selectable signals for further processing.

7. The receiver as claimed in claim 6, comprising a programmable memory operationally coupled to said trigger circuit and to a signal preconditioning circuit.

8. The receiver as claimed in claim 7, wherein said preconditioning circuit includes an input selector for selecting signals from any channel of said multi-channel signal transmitting and receiving means, a filter and a distance amplitude correction circuit.

9. A method for detecting and analyzing flaws in materials, comprising the steps of:
   transmitting signals in analog form towards a material and receiving signals reflected from, or transmitted through, said material, and
   converting the received analog signals into digital signals;
   dividing said digital signals into a multiplicity of separate, independent sections for selective evaluation of wave form portions as contained in each of said sections; and
   assigning a time value to a peak, or to a time associated with a zero-crossing following a peak, of a signal in each of said sections subjected to said selective evaluation.

10. The method as claimed in claim 9, further comprising the step of storing said received signals in digital form in a memory for subsequent processing.

11. A programmable receiver for analyzing flaws in a material, comprising:
   a trigger generator for transmitting signals in analog form to said material to be analyzed and for receiving the signals reflected from said material;
   an analog to digital converter connected to the trigger generator for converting the received signals into digital form;
   a raw data memory connected to said analog to digital converter for at least temporarily storing the digital signals from said converter;
   a time and amplitude processor connected to said analog to digital converter for identifying signal peeks and zero-crossing points;
   a time and amplitude memory connected to the time and amplitude processor for storing data processed in said time and amplitude processor; and
   circuit means for dividing said digital signals into a multiplicity of separate, independent sections for selective evaluation of waveform portions as contained in each of said sections.

* * * * *